United States Patent [19]
Hung et al.

[11] Patent Number: 5,653,974
[45] Date of Patent: Aug. 5, 1997

[54] PREPARATION AND CHARACTERIZATION OF LIPOSOMAL FORMULATIONS OF TUMOR NECROSIS FACTOR

[75] Inventors: Mien-Chie Hung, Houston, Tex.; Toshihiko Utsumi, Yamaguchi, Japan; Jim Klostergaard, Kingwood, Tex.

[73] Assignee: Board of Regents,The University of Texas System, Austin, Tex.

[21] Appl. No.: 351,002

[22] Filed: Nov. 30, 1994

Related U.S. Application Data

[63] Continuation-in-part of Ser. No. 923,110, Jul. 30, 1992, abandoned, which is a continuation of Ser. No. 599,811, Oct. 18, 1990, abandoned.

[51] Int. Cl.$^6$ .......................... A61K 9/127; A61K 38/19; C07K 1/113
[52] U.S. Cl. .......................... 424/85.1; 424/450; 530/351; 530/410
[58] Field of Search .................. 424/85.1, 450; 530/351, 403, 409, 410, 812; 930/144

[56] References Cited

U.S. PATENT DOCUMENTS

| | | | |
|---|---|---|---|
| 4,447,355 | 5/1984 | Sakamoto et al. | 424/85.1 |
| 4,457,916 | 7/1984 | Hayashi et al. | 424/85.2 |
| 4,650,674 | 3/1987 | Aggarwal et al. | 424/85.5 |
| 4,837,028 | 6/1989 | Allen | 424/1.21 |
| 4,879,226 | 11/1989 | Wallace et al. | 435/68.1 |
| 4,894,225 | 1/1990 | Zimmerman | 424/85.1 |
| 4,894,439 | 1/1990 | Dorin et al. | 530/351 |
| 4,948,875 | 8/1990 | Tanaka et al. | 530/350 |
| 4,963,354 | 10/1990 | Shepard et al. | 424/85.1 |
| 4,980,160 | 12/1990 | Goldberg et al. | 424/85.1 |
| 4,985,241 | 1/1991 | Zimmerman et al. | 424/85.1 |
| 4,987,237 | 1/1991 | Myers et al. | 549/222 |
| 4,990,455 | 2/1991 | Yamagishi et al. | 435/69.5 |
| 5,002,876 | 3/1991 | Sreekrishna et al. | 435/69.5 |
| 5,043,271 | 8/1991 | Yamada et al. | 435/69.5 |
| 5,059,421 | 10/1991 | Loughrey et al. | 424/417 |
| 5,059,530 | 10/1991 | Oshima et al. | 435/69.5 |

FOREIGN PATENT DOCUMENTS

| | | |
|---|---|---|
| A20247860 | 12/1987 | European Pat. Off. . |
| 0338679 | 10/1989 | European Pat. Off. . |
| 3913791 | 10/1990 | Germany . |
| 2042360 | 2/1990 | Japan . |
| WOA19106560 | 5/1991 | WIPO . |

OTHER PUBLICATIONS

Journal of Lipid Research, vol. 8, issued 1967, Lapidot et al., "Use of esters of N–hydroxysuccinimide in the synthesis of N–acylamino acids", pp. 142–145.

(List continued on next page.)

*Primary Examiner*—Jeffrey E. Russel
*Assistant Examiner*—Kathleen Carroll
*Attorney, Agent, or Firm*—Arnold, White & Durkee

[57] ABSTRACT

A tumor necrosis factor (TNF) preparation with high cytolytic activity is described. The TNF preparation includes modified forms of TNF associated with or encapsulated within liposomes. The TNF molecule is modified at up to 3 amino acid residues per trimer with nearly complete retention (80–95%) of biological activity. Amino acid residues of the TNF are modified to include long chain fatty acids via TNF lysyl side chains and/or N-terminal amino acid groups. The disclosed modified TNF molecules provide a highly efficient method for preparing liposome-associated or encapsulated TNF complexes in either standard multilamellar vesicles (MLVs) or small unilamellar vesicles (SUVs) having enhanced in vivo stability. The liposomes of the present invention feature particularly small diameters in the range of 0.02–0.05 um in diameter. The binding of the modified TNF molecules to the surface of SUVs is up to 100% efficiency. Pharmacologically acceptable preparations of modified TNF for the particular treatment of TNF-responsive tumors are also provided. Methods of preparing liposomal-lipophilic TNF molecules are provided. Highly efficient methods of preparing stable, surface-associated protein liposome complexes having enhanced stability in vivo are also provided.

41 Claims, 14 Drawing Sheets

Cell Killing Activity of C8-Biogen-DSPC-liposomal TNF

OTHER PUBLICATIONS

Decker, T. et al. (1987), "Cell–Associated Tumor Necrosis Factor (TNF) as a Killing Mechanism of Activated Cytotoxic Macrophages," *J. Immunol.*, 138 (3):957–962, printed in the United States.

Espevik, T. and Nissen–Meyer, J. (1987), "Tumour Necrosis Factor–Like Activity on Paraformaldehyde–Fixed Monocyte Monolayers," *Immunol.*, 61:443–448, published in Europe.

Bakouche et al (1988), "Plasma Membrane–Associated Tumor Necrosis Factor: A Non–Integral Membrane Protein Possibly Bound to Its Own Receptor," *Jour. of Immunol.*, 140(4):1142–1147, published in USA.

Kriegler et al (1988), "A Novel Form of TNF/Cachectin Is a Cell Surface Cytotoxic Transmembrane Protein: Ramifications for the Complex Physiology of TNF," *Cell*, 53;45–53, published in USA.

Debs et al (1989), "Liposome–Associated Tumor Necrosis Factor Retains Bioactivity in the Presence of Neutralizing Anti–Tumor Necrosis Factor Antibodies," *Journal of Immunol.*, 143(4):1192–1197, published in USA.

Debs et al (1990), "Immunomodulatory and Toxic Effects of Free and Liposome–Encapsulated Tumor Necrosis Factor $\alpha$ in Rats," *Cancer Research*, 50:375–380, published in USA.

Utsumi et al (1988), "Association of a Myrisotylated Protein with a Biological Membrane and Its Increased Phosphorylation by Protein Kinase C," *FEBS Letters*, 238(1):13–16, published in Europe.

Utsumi et al (1990), "Correlation Between Membrane Binding and Phosphorylation by Protein Kinase C of Acylated Protein," *Agric. Biol. Chem.*, 54(1):25–30, published in Japan.

Ando et al (1988), "Synthesis of Acylated SOD Derivatives Which Bind to the Biomembrane Lipid Surface and Dismutate Extracellular Superoxide Radicals," *FEBS Letters*, 240 (1,2):16–220, published in Europe.

Terada et al (1988) "Myristoylation of Neutrophil Proteins and Their Biological Characteristics," *Cell Structure and Function*, 13:359–371, published in Japan.

Utsumi et al (Nov. 21, 1990), "Preparation and Characterization of Liposomal Lipd–Linked TNF Formulations," *3rd International Conference on Tumor Necrosis Factor and Related Cytokines*, abstract #P3–21;153, published in Japan.

Aggarwal et al. (1985), "Human Tumor Necrosis Factor," *Methods in Enzymology*, 116:448–457, published in USA.

Klostergaard et al. (1985), "Induction and Characterization of Lymphotoxins from Tumor Promoter Synergized Lectin––Stimulated Human Lymphocytes in Vitro," *Biological Abstracts*, 80(5): Abstract 40216, p. AB–403, published in USA.

Klostergaard et al. (1987), "Tumoricidal Effector Mechanisms of Murine Bacillus Calmette–Guerin–Activated Macrophages: Mediates of Cytolysis, Mitochondrial Respiration Inhibition, and Release of Intracellular Iron by Distinct Mechanisms," *Chemical Abstracts*, 106(25): Abstract 212340T, p. 521, published in USA.

Klostergaard et al. (1987), "Monokine Mediated Release of Intracellular Iron in Tumor Target Cells in Vitro," *Chemical Abstracts*, 106(13): Abstract 100662T, p. 517, published in USA.

Klostergaard, J. (1987), "Monokine Mediated Release of Intracellular Iron in Tumor Target Cells In Vitro," *Lymphokine Research*, 6:19–28, published in USA.

Klostergaard et al. (1987), "Tumoricidal Effector Mechanisms of Murine Bacillus Calmette–Guerin–Activated Macrophages: Mediation of Cytolysis, Mitochondrial Respiration Inhibition, and Release of Intracellular Iron by Distinct Mechanisms," *Cancer Res.*, 47:2014–2019, published in USA.

Klostergaard et al. (1985), "Induction and Characterization of Lymphotoxins from Tumor Promoter–Synergized, Lectin–Stimulated Human Lymphocytes In Vitro," *Journal of Biological Response Modifiers*, 4:195–209, published in USA.

Klostergaard et al. (1987), "Tumoricidal Effector Mechanisms of Murine BCG–Activated Macrophages. I. Parameters of Production and Initial Characterization of a Cytolytic Factor Serologically Related to Necrosin," *Journal of Biological Response Modifiers*, 6:313–330, published in USA.

Patent Cooperation Treaty Search Report, PCT/US91/07694, mailed Mar. 12, 1992.

Utsumi, T. et al. (Jul. 1, 1991), "Preparation and Characterization of Liposomal–Lipophilic Tumor Necrosis Factor", *Cancer Res.*, 51(13):3362–3366, published in USA.

Lam, K.S. et al., (1988), "Analysis of the Molecular Organization of Recombinant Human Tumor Necrosis Factor (rTNF) in Solution Using Ethylene Glycolbis (succinimidylsuccinate) As the Cross–Linking Reagent," *J. Biol. Response Mod.*, 7(3):267–275, published in USA.

Smith, R.A. et al. (May 25, 1987), "The Active Form of Tumor Necrosis Factor is a Trimer," *J. Biol. Chem.*, 262(15):6951–6954, published in USA.

Mamoru et al., (1990), "ATL Antibody Measuring Reagent," Search report directed to Japanese patent, JP2042360.

White et al., "The Lipids," *Principles of Biochemistry*, Sixth Edition, Chapter 3, pp. 38–44, McGraw–Hill Book Company, publishers, published in USA. (1978).

Takada et al., (1985), "Immunopharmacological Activities of a Synthetic Counterpart of a Biosynthetic Lipid A Precursor Molecule and of Its Analogs," *Infection and Immunity*, 48(1):219–227, published in USA.

Lodato et al., "Hemodynamic Evaluation of Recombinant Human Tumor Necrosis Factor (TNF)–$\alpha$, TNF–$SAM_2$ and nLiposomal TNF–$SAM_2$ in an Anesthetized Dog Model," *J. Immunol.*, 17:19–29, 1995.

Klostergaard et al., "Improved therapeutic index of a liposomal lipophilic tumor necrosis factor mutant," Proceedings of the American Association for Cancer Research, Apr. 10–13, 1994, San Francisco, CA, p. 520, abstract No. 3098.

PREPARATION AND CHARACTERIZATION OF LIPOSOMAL FORMULATIONS OF TUMOR NECROSIS FACTOR

CROSS REFERENCE TO RELATED APPLICATIONS

The present application is a continuation-in-part application of prior application U.S. Ser. No. 07/923,110 filed Jul. 30, 1992, now abandoned; filed as a continuation of U.S. Ser, No. 07/599,811 filed Oct. 18, 1990 (now abandoned).

BACKGROUND OF THE INVENTION

1. Field of the Invention

The present invention relates to the field of chemically modified forms of tumor necrosis factor (TNF) and uses thereof in the inhibition of tumor growth. In that the present invention presents novel forms of TNF, the invention also relates to methods of producing the modified TNF forms described. In that TNF is able to demonstrate anti-tumor cell activity, the present invention also provides methods of inhibiting tumor growth and treating TNF responsive cancers in humans.

2. Background of the Invention

Tumor necrosis factor (TNF) has become the recent focus of intense interest because of evidence for its role in a wide range of physiological mechanisms, immunopathologies, immunomodulation, and as a potential anti-neoplastic agent.[20] In the last few years following the cloning of its cDNA,[21-24] many diverse studies have begun to elucidate features of its structure, including x-ray crystallography and development and characterization of variants with altered primary sequence.[26-31]

Studies involving specific molecular modifications of the TNF molecule have proceeded despite scant prior evidence for the critical functional role of particular types of amino acid side-chains in TNF. Nevertheless, positively charged arginyl[26] and lysyl[25] residues have been shown or surmised to exert important effects on activity and/or three-dimensional structure. For example, introduction of arginyl residues as conservative or nonconservative substitutions in the N-terminal region of rHuTNF has been demonstrated to confer favorable effects on tumor cytotoxicity in vitro and to diminish toxicity in animal models.[26-28] Furthermore, lysyl residues have been proposed to participate in intra- and inter-molecular interactions with other amino acid side-chains in the rHuTNF trimer.[25]

rHuTNF is a homotrimer of 17 kD subunits, each of which contains an N-terminal valine and six lysyl residues; two of these lysyl residues are known to be involved in intra- or intersubunit interactions.[25] TNF has been characterized as being cytotoxic for some tumor cell lines in vitro and as effective in causing necrosis of certain tumors in vivo.[12,32] This phenomenon was first described late in the last century when physicians noted rare spontaneous regressions of tumors in cancer patients.

However, TNF has also been shown to be a critical factor involved in the onset of septic shock.[12] In addition, TNF is identical to cachectin, a serum borne factor associated with cachexia, an emaciated condition of the body associated with chronic illness.[13,33] However, the tumor cytotoxic activity of TNF continues to prompt researchers to develop TNF preparations having reduced dose-limiting side effects with the greatest retention of tumor cytolytic activity.

For example, TNF has already become the subject of initial evaluation in Phase I/Phase II clinical trials at institutions worldwide.[34-37] However, the major impediment to further development remains in the described dose-limiting hypotension, perhaps-due to direct effects on vascular endothelium.[38-41] A strategy to better localize this cytokine in the tumor microenvironment and to diminish its systemic accessibility to normal tissue would thus provide a major advancement in the potential use of this valuable pharmaceutical agent in vivo.

Liposomes are emerging into early clinical evaluation as non-toxic drug carriers. They appear particularly well suited as carriers for hydrophobic drugs. At the same time, liposomes may target drugs directly to reticuloendothelial cell-rich organs, such as lung and liver, and indirectly to tumor beds via RES-mediated trafficking. The latter may be a particularly effective strategy in the use of TNF, as some reports indicate intratumoral administration is the most effective route.

However, native TNF demonstrates low encapsulation or association efficiencies for liposomes as reported in prior studies.[5,6] For example, in the inventor's own laboratory, TNF encapsulation efficiencies were poor with native TNF and acylated TNF. In particular, native TNF bound liposomes with an efficiency of only 3.9% to preformed MLVs of PG/cholesterol, and from only 2.0–11.4% with ML's of mixtures of phosphatidylcholine (PC) phosphatidyl glycerol (PG), phosphatidyl serine (PS) and cholesterol (Chol). It is theorized that this poor affinity is due primarily to TNF's relatively low hydrophobicity.

More efficient methods of preparing liposome-associated TNF would be of significant medical value in the use of this agent as a therapeutic tool in the clinical management of cancer and other conditions, as well as greatly expand the scope of use to which TNF may be employed. Persons restricted from receiving TNF because of conditions potentially exacerbated by this agent may have TNF become available to them if the TNF hypotensive tendencies and other toxic side effects could be reduced and/or eliminated. More efficient methods for coupling TNF to liposomes pose a potential solution to reducing the toxic side effects of TNF.

SUMMARY OF THE INVENTION

The present invention relates to the particular preparation and characterization of unique liposomal formulations of TNF, referred to herein as lipophilic TNF preparations. The inventors have hypothesized that monocyte/macrophages possess the ability to preferentially kill tumor cells using a membrane form of TNF.[42-46] However, host toxicities associated with the systemic use of TNF, such as hypotension and systemic shock, have limited the potential use of this otherwise valuable peptide as a therapeutic agent in humans.[38]

Applicants present herein a method by which the host toxicities associated with TNF may be significantly reduced and/or eliminated. Such is accomplished through the specific modification of the TNF molecule to include fatty acids, and the advantageous and efficient association of these modified TNF with liposomes. The liposomes of the present invention are characterized herein as either small unilamellar vesicles (SUV) or multilamellar vesicles (MLVs).

According to the present invention, a modified TNF molecule having essentially completely retained cytolytic activity wherein amino residues of the tumor necrosis factor has been modified, is disclosed. More particularly, TNF modified at less than 5 amino residues per TNF trimer have been prepared with successful retention of cytolytic biological activity. Even more particularly, data collected in inventor's laboratory demonstrates TNF modified at between about 1–3 amino residues to include fatty acids are described which have almost complete retention of native TNF cytolytic activity.

The amino residues of the TNF molecule which may be modified according to the present invention include the N-terminal amino group or lysine amino residues of the TNF molecule. These amino residues become reactive and facilitate the attachment of other chemical groups, such as fatty acids, to the TNF structure. The attachment of fatty acids to the modified TNF enhances the hydrophobicity of the TNF, thereby facilitating the efficient and highly stable association of the TNF to liposomes.

In a preferred embodiment of the claimed modified TNF preparations, the referenced modified amino residues of the tumor necrosis factor is a molecule lysine amino residue or an N-terminal amino residue. Where the amino residue of choice is lysine group (i.e., lysyl residue), lysyl side chains function as attachment sites for fatty acids to the tumor necrosis factor molecule. In these particular most preferred embodiments of the described amino residue modified TNF preparations, the fatty acid-modified TNF complex comprises a lipophilic TNF preparation. The bioactivity of these lipophilic TNF preparations is demonstrated by the inventors to retain essentially full cytolytic activity as compared to unmodified forms of native TNF.

The inventors also disclose herein a novel and highly stable methodology for preparing the described lipophilic modified TNF molecules in association with the surface or encapsulated within a liposome. In such association, the TNF preparation comprises liposomal lipophilic TNF. The association of modified lipophilic TNF with liposomes (i.e., surfaces and encapsulated) has been found to occur with surprisingly enhanced efficiency. Binding of the fatty acid at the TNF molecule is demonstrated to occur with the surface of the liposomes with at least 50% efficiency. Additionally, the high binding efficiencies further suggest that the liposomal preparations may be highly stable in vivo. Stability as used herein to describe liposomal-TNF refers to a decrease or a decreased tendency of the TNF-liposome to leak TNF (i.e., renter free TNF) into the system in vivo.

In even more particularly defined aspects of the invention, the liposome may comprise an SUV or an MLV. The described SUVs of the present invention most preferably have a diameter of between 0.02–0.05 μm. Even more preferably, the liposomes and SUVs of the present invention are comprised of a neutral lipid, most particularly these neutral lipids include, by way of example, DPPC or DSPC. SUVs comprised of neutral lipids (DPPC or DSPC) advantageously impart the feature of reduced RES—mediated clearance rates in vivo compared to MLVs. The inventors submit the described modified TNF molecules may advantageously associate with the surfaces of the liposome (i.e., SUV or MLV), or become encapsulated within a liposome (MLV), to form a highly stable complex in vivo. The inventors have already demonstrated that these formulations form highly stable complexes in vitro.

In most particularly preferred embodiments of the claimed invention, the TNF comprises a recombinant human TNF (rHuTNF). These particularly preferred embodiments of the invention comprise an rHuTNF preparation having modified amino residues. In a particularly preferred aspect of this embodiment, less than 5 amino residues are modified per TNF trimer. Even more particularly, between about 1–3 amino residues per TNF trimer are modified with essentially complete retention of cytolytic activity. The described amino residues are most preferably further modified to include fatty acids, most preferably long chain fatty acids. As used in the specification, long chain fatty acids refer to those fatty acids having a carbon chain length of between 8 and 14 carbon atoms, inclusively. The described rHuTNF preparations are capable of associating with a liposome, most particularly, the surface of a liposome, with essentially 100% binding efficiency. The described rHuTNF preparations, similarly, are characterized by an essentially full complement of native TNF cytolytic biological activity.

The present invention also provides a method for preparing liposomal lipophilic TNF, said method providing between 50% and 100% liposome—TNF binding efficiency. In contrast, native TNF or acylated TNF was found to bind with very poor efficiency.

Any variety of chemical methods known to those of skill in the art to associate a fatty acid to a protein may be used to prepare the TNF lipid adducts of the present invention, albeit with various degrees of coupling efficiency. However, a most preferred method for preparing the liposomal lipophilic TNF comprises the steps of reacting an amount of TNF with a sufficient amount of an N-hydroxysuccinimide ester of a fatty acid for an amount of time sufficient to form an amount of an lipophilic TNF preparation; formulating a volume of liposomes capable of binding lipophilic TNF molecules with high efficiency; and incubating a volume of the liposomes with a sufficient amount of lipophilic TNF preparation an amount of time sufficient for the lipophilic TNF to bind the liposomes, thereby providing a formulation of liposomal lipophilic TNF.

Most preferably, the particular TNF to be employed in the claimed method comprises a recombinant human TNF (rHuTNF). Even more particularly, the described method employs fatty acids having a carbon length of between 8 to 14 carbon atoms, inclusive. Fatty acid chain lengths of about 8 carbons in length are most particularly preferred. Fatty acids having a carbon chain of 14 or greater carbon atoms typically cause lower recovery (i.e., protein insolubilization) and greater loss of biological (cytolytic) activity of the TNF.

In order to provide the lipophilic TNF preparation, the TNF is reacted with the N-hydroxysuccinimide esters of the described fatty acids for about 3 hours at about 26° C. In an even more particularly defined aspect of the claimed method, the liposomal lipophilic TNF preparation comprises a ratio of about 0.5 moles TNF per mole of liposomal preparation. Molar ratios higher than about 0.5 moles TNF to mole of liposome preparation may also advantageously provide the described and claimed liposomal lipophilic TNF preparations.

In still another preferred embodiment of the claimed invention, a pharmacologically acceptable preparation of TNF is provided. This pharmacologically acceptable preparation of TNF is more specifically defined as comprising modified TNF molecules associated with a liposome. According to one aspect of this preparation, the TNF is associated with liposome surfaces. This surface-association is facilitated through the inclusion of fatty acids at the amino residues of the TNF structure. The reactive amino groups of the TNF molecule provide the attachment sites for these fatty acids.

Most preferably, the liposomes of the pharmacologically acceptable preparation described herein are defined as SUV having a diameter of about 0.02 to 0.05 μm. SUV-TNF preparations are most particularly well suited for the treatment of patients wherein there is relatively low phagocytic cell infiltration of a tumor mass. Trafficking of SUV-TNF through normal routing (endothelial cells and so forth) may then direct the delivery of TNF to a targeted tumorous tissue. Alternatively, MLV-TNF preparations may be used, and may be preferred for the treatment of patients having tumors highly infiltrated with phagocytic cells. MLV-TNF preparations may more readily be captured by phagocytic cells, which may then traffic the liposomal-lipophilic TNF to a tumorous tissue. By either preparation, a reduction in systemic toxicity may be provided by the more highly efficient association of the modified and highly hydrophobic TNF to the liposome, thereby reducing the amount of non-liposomal bound TNF in the preparation and in the dose being administered.

The TNF of the preparation is modified at amino residues to include the referenced fatty acids. More specifically, less than 5 amino residues per TNF trimer are modified. Even more preferably, between about 1-3 amino residues of the TNF trimer are modified in the described pharmacologically acceptable TNF preparation.

The fatty acids employed in preparing the described pharmacologically acceptable preparations of TNF are more particularly described as having a carbon chain length of between 8 to 14 carbons. By way of example, the fatty acid is caprylic acid, capric acid, lauric acid or myristic acid, as well as modifications and variations of fatty acids having a carbon chain length of between 8 to 14 carbons. In a most particularly preferred embodiment of the claimed pharmacologically acceptable preparations, the particular fatty acid associated with the TNF is caprylic acid. In this particular embodiment, about 3 amino residues of the TNF molecule include the described caprylic acid addition at modified TNF amino residues.

In still another important embodiment, the invention provides a method for treating a tumor in a patient. This method comprises identifying a patient having a TNF receptive tumor; administering to the patient a tumor-inhibiting dose of a liposomal lipophilic modified TNF preparation; and treating the patient with daily tumor-inhibiting doses of the liposomal lipophilic modified TNF until an improvement in the patient's condition is detected. This method is hypothesized to facilitate spontaneous tumor regression and disintegration, as well to slow and/or halt tumor growth in TNF responsive patients.

More particularly, the liposomal lipophilic modified TNF included in the claimed method comprises a TNF molecule modified at less than 5 amino acid residues to include a fatty acid, the particular fatty acid comprising a carbon chain length of between 8 to 14 carbons, inclusive. Even more preferably, between about 1-3 of the amino residues of the TNF trimer are modified to include a fatty acid. The TNF associated fatty acid most preferably has a carbon chain length of about 8 carbons. This particular fatty acid is caprylic acid. The liposomes are most preferably described as SUV or MLV, or a mixture of MLV and SUV, comprised of neutral lipids. The most preferred neutral lipids for use in the described pharmacologically acceptable formulation are the phospholipids. By way of example, the phospholipid may comprise DPPC or DSPC.

The described preparation is postulated to have a significantly reduced host toxicity, perhaps due to the reduced amount of available free TNF (i.e., higher efficiency for binding TNF to liposomes, less TNF leakage from liposomes (higher in vivo stability)). Therefore, while any mode of administration is considered to be applicable for use in the described method, a particularly noted embodiment of the invention is administration via systemic administration. Another embodiment of note is regional administration, particularly as a means of enhancing intratumoral delivery.

The term modified as used herein encompasses any chemical modification of the N-terminal amino residue or any of the lysine residues of the TNF molecule which would facilitate the attachment of chemical groups to the TNF molecule, the chemical groups which may be attached to these modified amino residues function to increase or enhance the hydrophobicity of the TNF. Even more particularly, these chemical groups are fatty acids.

Modification of TNF to include these chemical groups may be accomplished by a number of methods well known to those of skill in the art for the attachment of a fatty acid to a protein. By way of example, methods which could be used for this purpose include the chemical modification of reactive TNF amino functions by nucleophilic substitution with an N-hydroxysuccinimide ester of the fatty acid, by use of a fatty acid anhydride, by use of a fatty acid chloride or by use of a carbodiimide coupling method. The method most preferred and found most successful in providing high coupling efficiencies with TNF is the nucleophilic substitution with an N-hydroxysuccinimide ester of the fatty acid.

The following abbreviations are employed throughout the Specification:

SUV=small unilamellar vesicle

RES=reticuloendothelial seplem

TNF=tumor necrosis factor

MLV=multilamellar vesicles

DPPC=dipalmitoyl phosphatidyl choline

DSPC=distearoyl phosphatidyl choline

DPPC-SUV-$C_8$-TNF=liposomal lipophilic TNF modified with caprylic acid associated with small unilamellar vesicles made of dipalmitocyl phosphatidyl choline.

4(b) Effect of increasing extent of amino group modification on recovery (solubility) of TNF in aqueous buffer.

Figure 5:
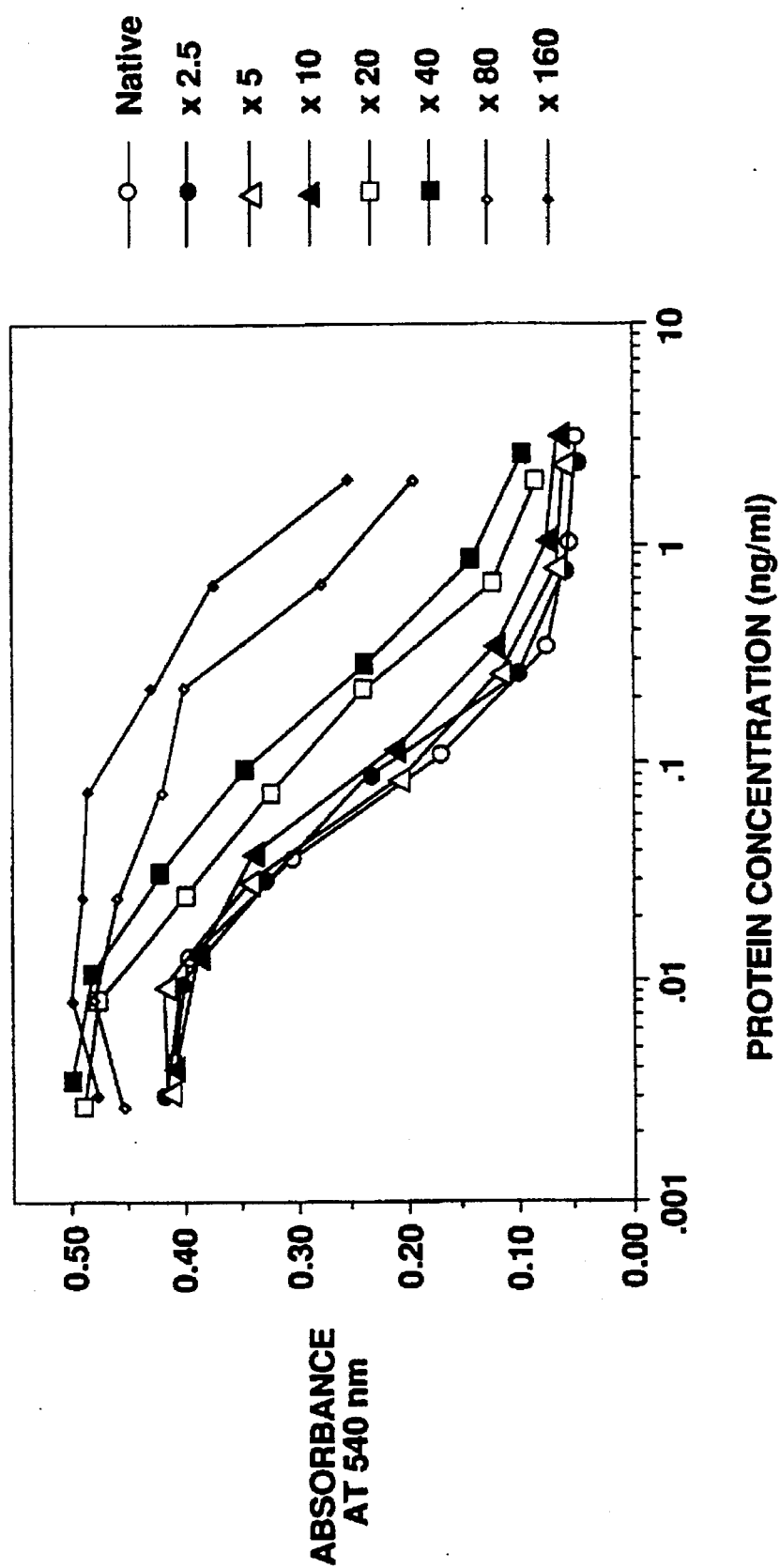

FIG. 5 Dose response curves for the cytolytic activity of acetylated TNF. Acetylated TNF with different levels of modified amino residues were subjected to biological assay on actinomycin D-treated L-929 cells. Absorbance of incorporated dye was measured at 540 nm and was plotted against the TNF concentration. This graph demonstrates the decrease in biological activity of the TNF molecule upon acetylation with greater than about 3 amino residues (i.e., 2.2 acetylated amino residues) per TNF trimer.

Figure 6:
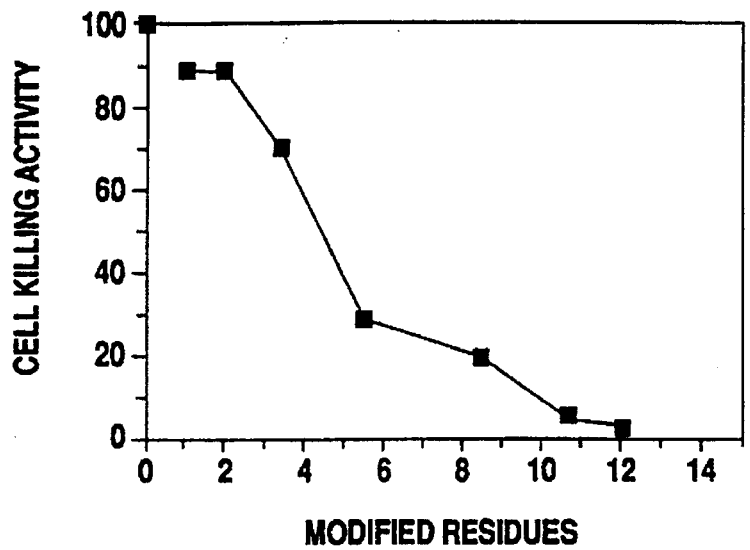

FIG. 6 Dose response curve for cytolytic activity of acetylated TNFs against extent of acetylation. The graph demonstrates a significant decrease in cell killing activity of TNF after acetylation with greater than about 3 amino residues. For example, with acetylated TNF having 4 modified amino residues, the cell killing activity of the compound was approximately 70%.

Figure 7A:
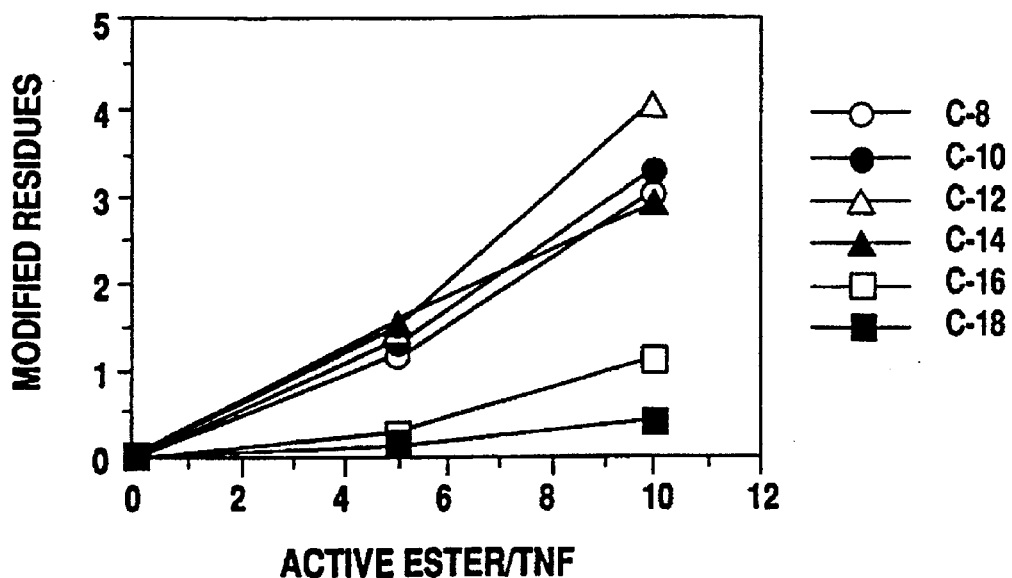
Figure 7B:
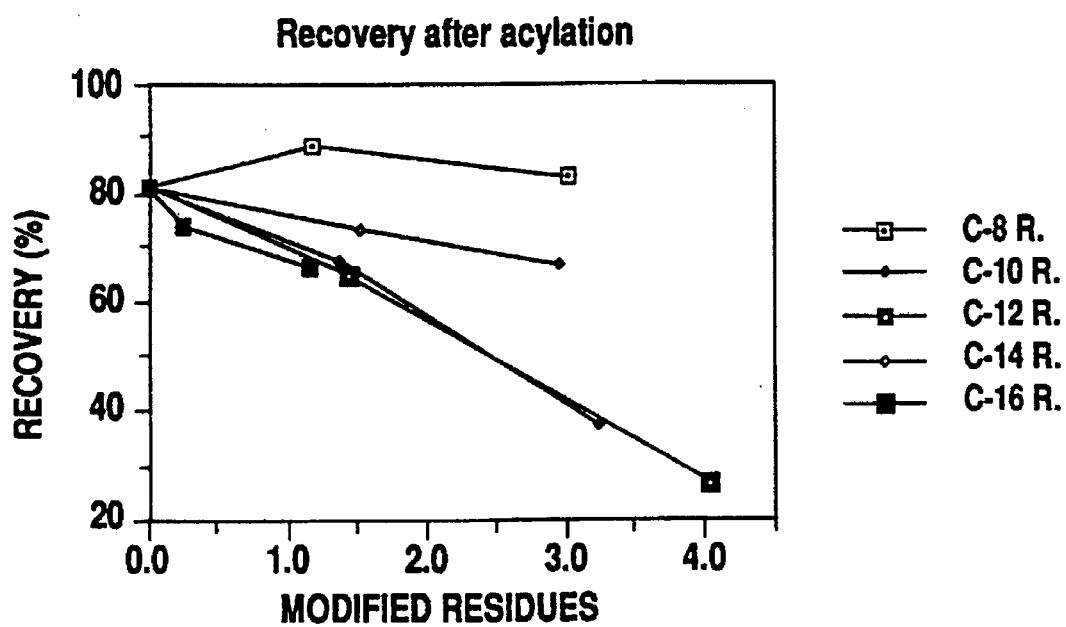

FIG. 7–7(a) Effect of mole ratio of active ester to TNF used for acylation and fatty acid chain length on the extent of modification.

7(b) Effect of fatty acid chain length and extent of substitution on recovery (solubility) of TNF in aqueous buffer.

Figure 8:
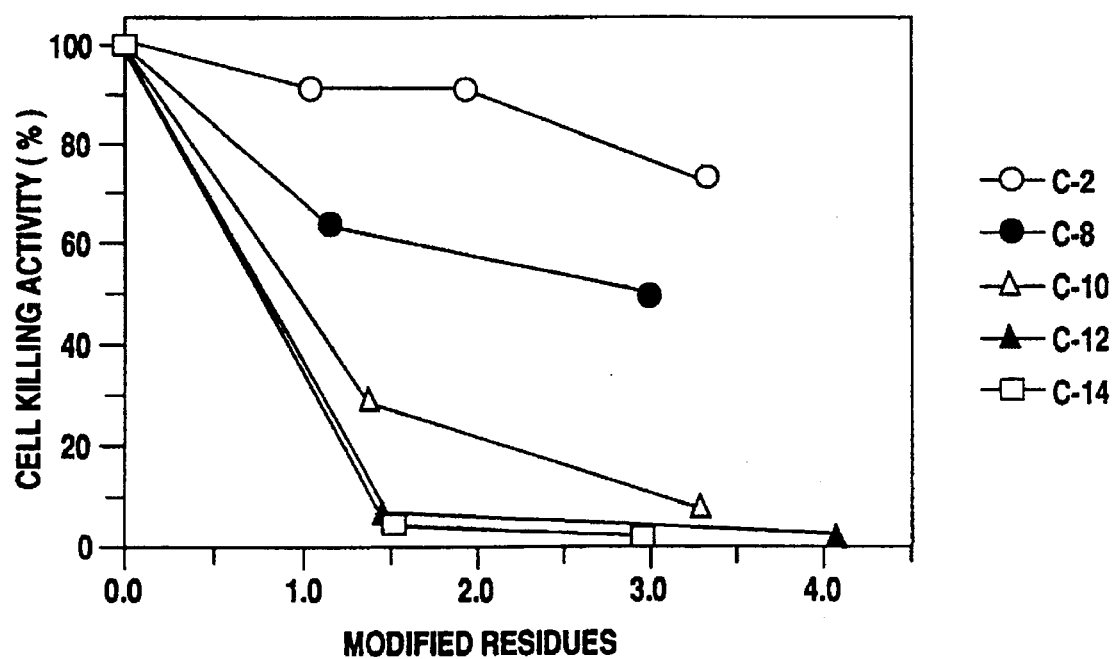

FIG. 8 Effect of extent of substitution and fatty acid chain length on biological activity on TNF.

FIG. 9 Binding of $^{125}$I-native and $C_2$ TNF (9a); and $C_8$ TNF and $C_{14}$-TNF (9b) to DPPC-SUVs. Reaction mixtures were separated by molecular sieving: SUVs appear in void volume (Arrow).

Figure 10:
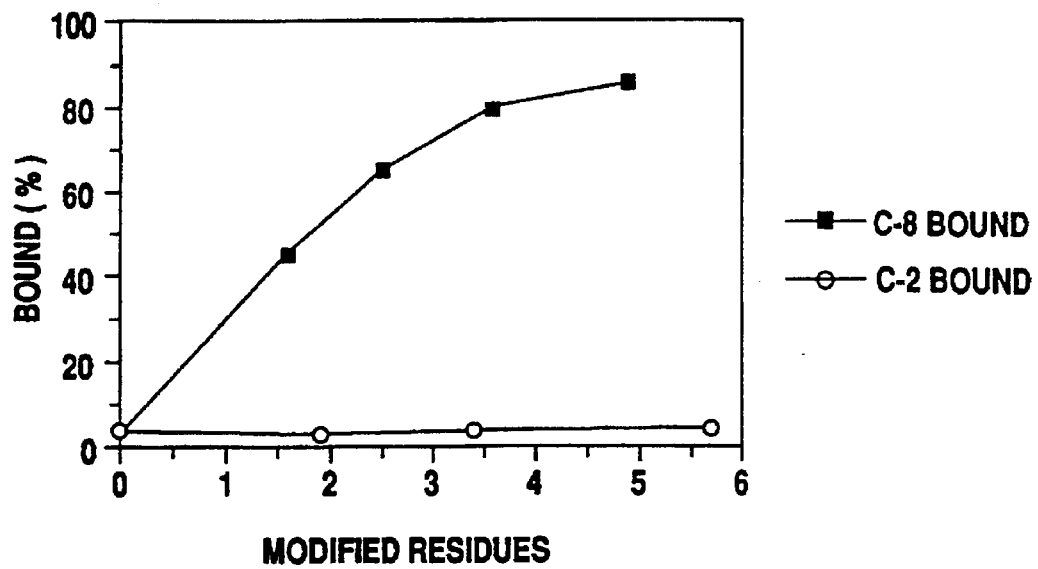

FIG. 10 Effect of extent of modification of TNF with $C_2$- or $C_8$-chains on binding to DPPC-SUVs.

Figure 11:
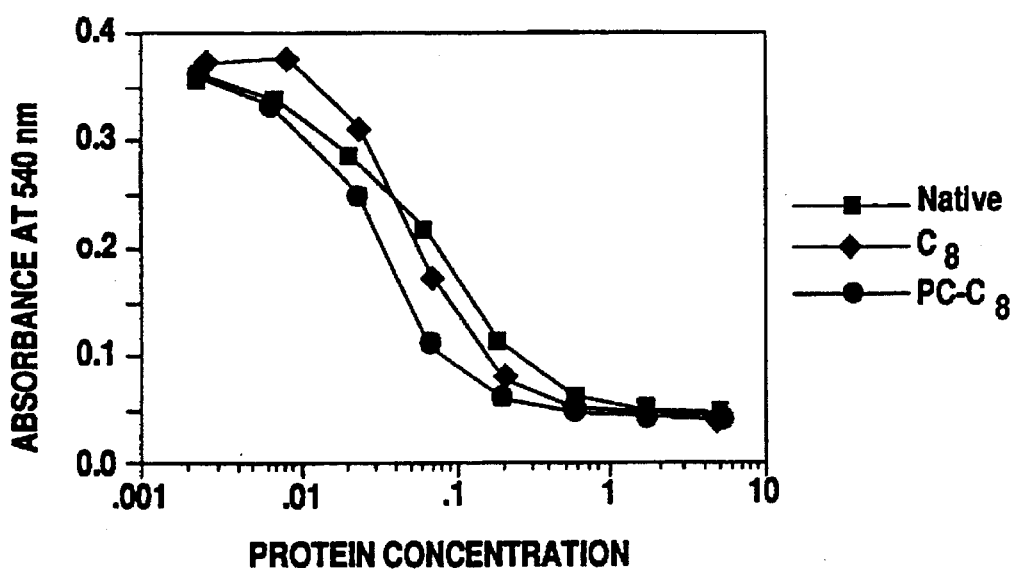

FIG. 11 Biological activity of native, $C_8$- and DPPC-SUV-$C_8$-TNF: Dose-response curve for neutral red incorporation by L929 targets against protein-concentrations.

Figure 12A:
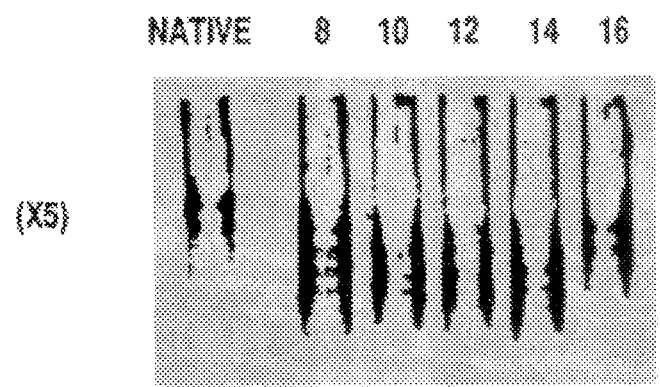
Figure 12B:
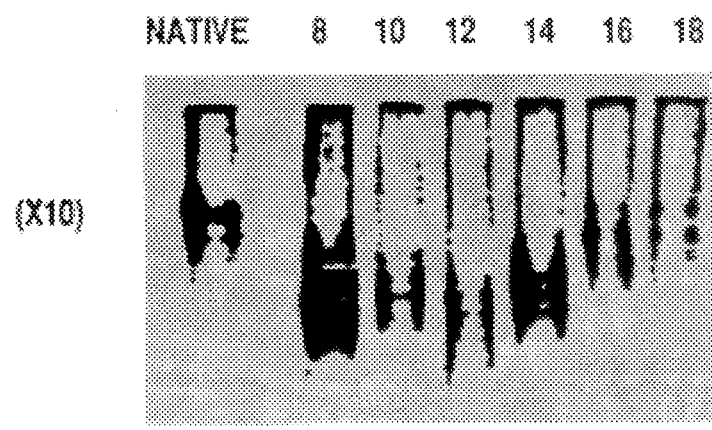

FIG. 12 C8–C18 Acylation of TNF. Native PAGE analysis of rHuTNF reacted with 5X or 10X molar ratios of $C_8$ to $C_{18}$-active esters.

Figure 13A:
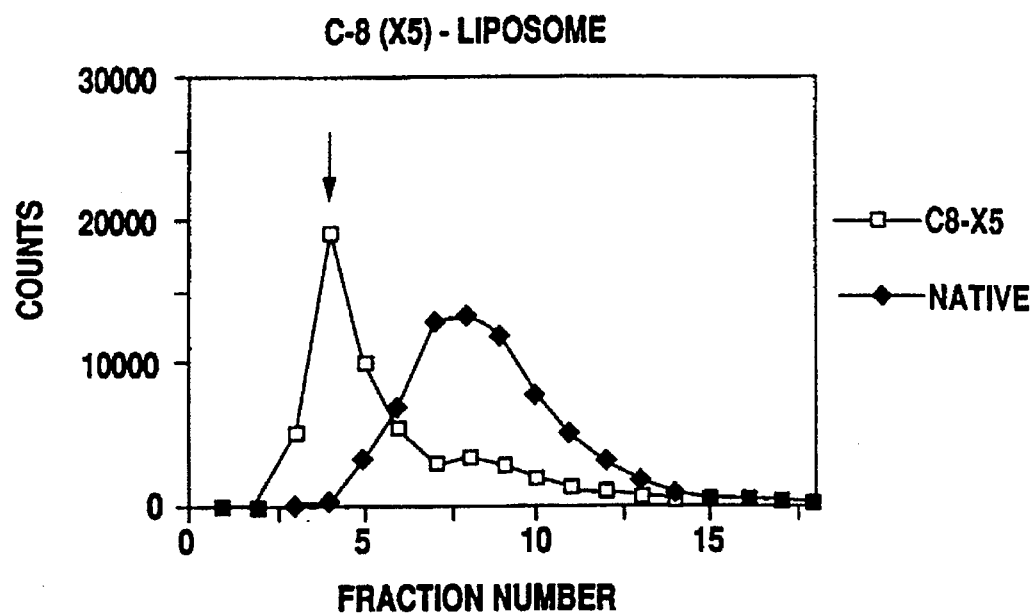
Figure 13B:
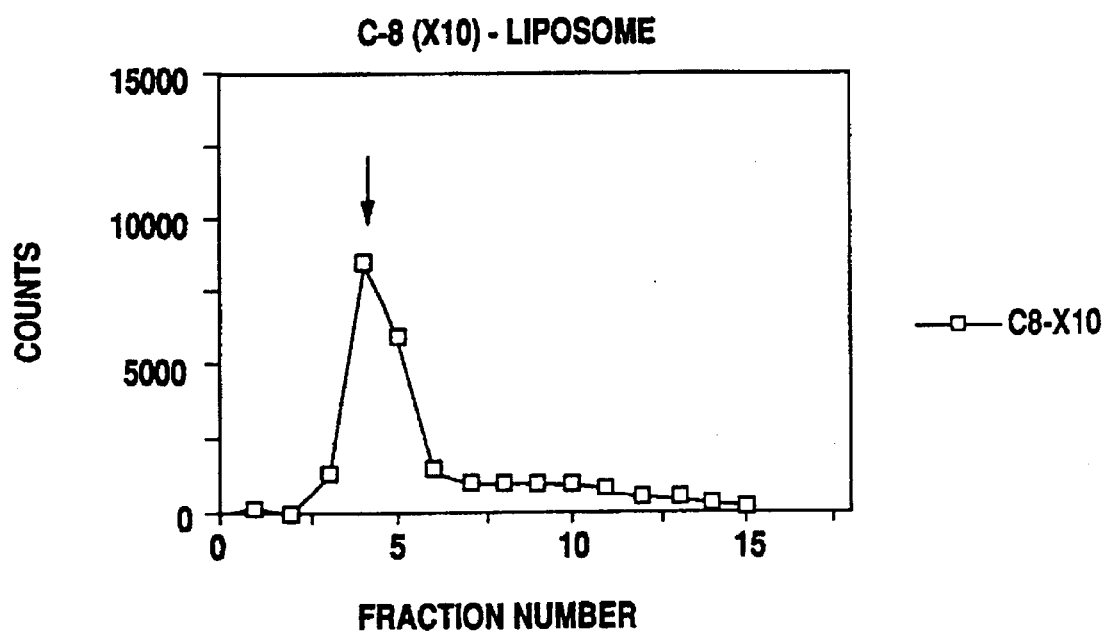

FIG. 13–13(a) C8(X5)-TNF-Liposome. Molecular sieving on Sephadex G-200 of DPPC-SUV reacted with native (unmodified) TNF or TNF reacted with a 5X molar ration of $C_8$ active ester. Arrow indicated void volume marker and sample subjected to bioassay (□=C8-X5; ♦=Native TNF).

13(b) C8(X10)-TNF-Liposome. As per FIG. 13(a), except that TNF reacted with a 10X molar ratio of $C_8$ active ester was used (□=C8-X10).

Figure 14A:
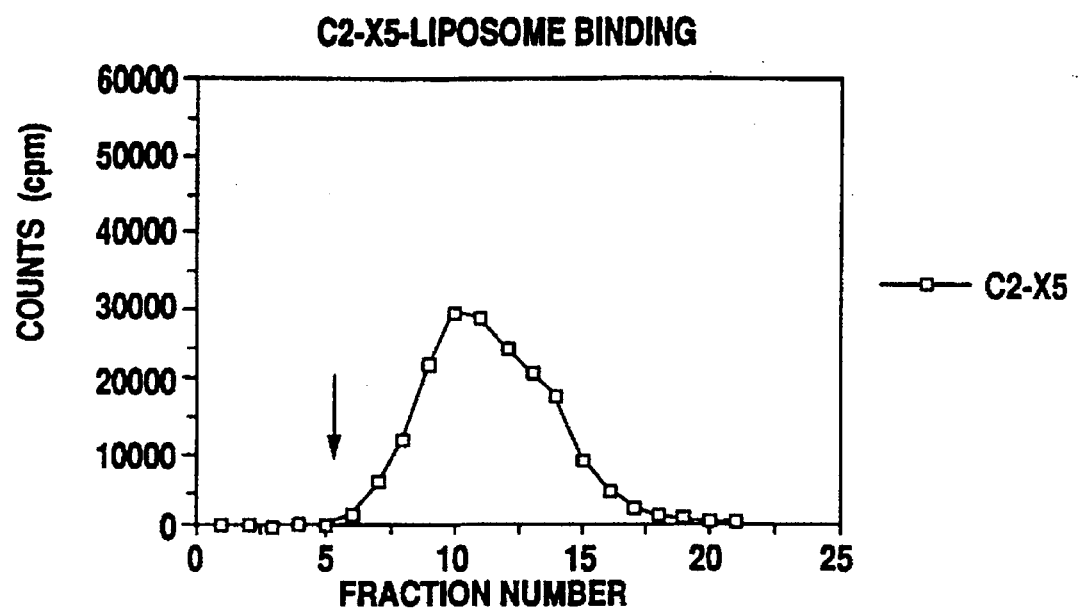
Figure 14B:
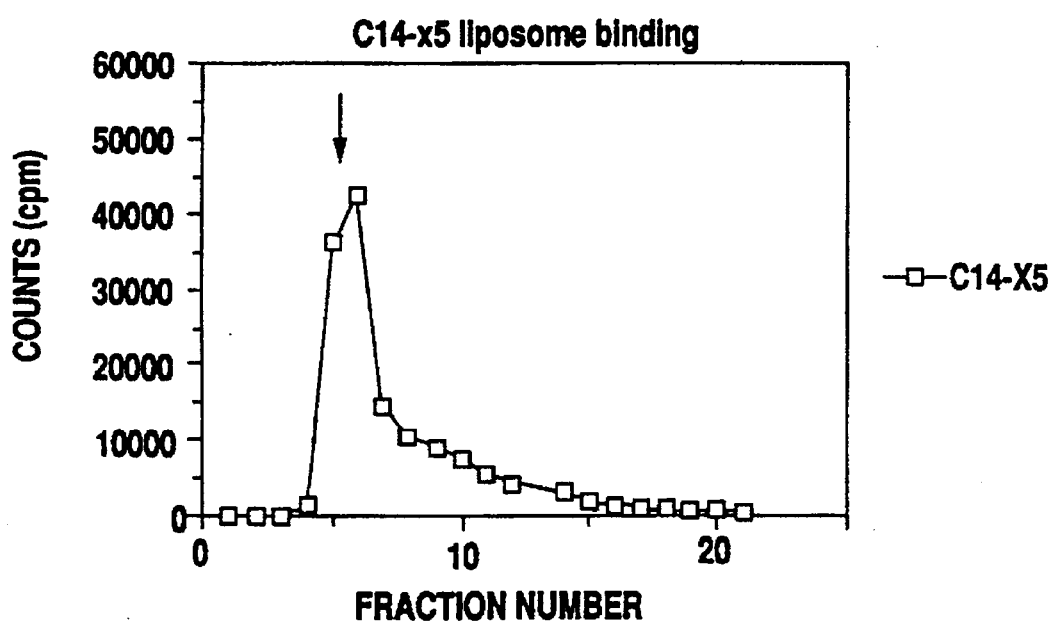
Figure 14C:
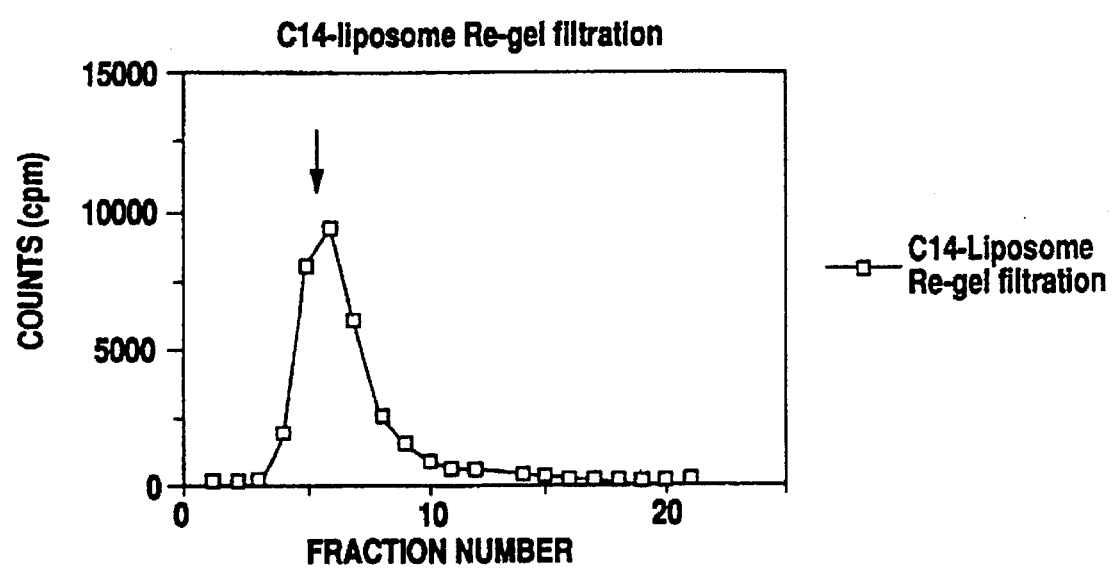

FIG. 14(a) C2-5X Liposome Binding. As per FIG. 13(a), except that TNF reacted with a 5X molar ratio of $C_2$ active ester was used.

14(b) C14-5X Liposome Binding. As per FIG. 13(a), except that the TNF reacted with a 5X molar ratio of $C_{14}$ active ester was used.

14(c) C14-Liposome Re-gel filtration.

Figure 15A:
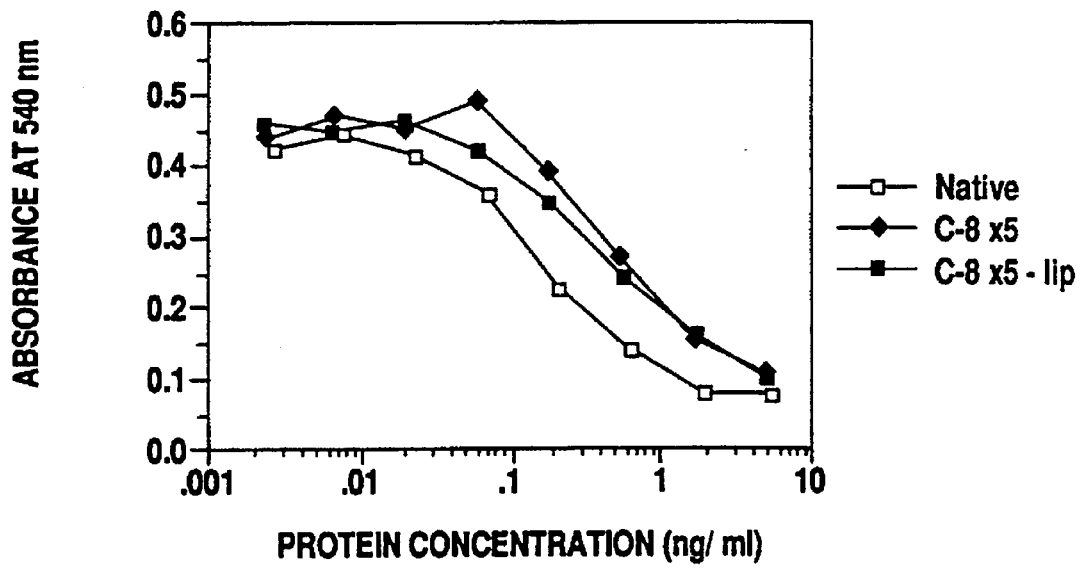
Figure 15B:
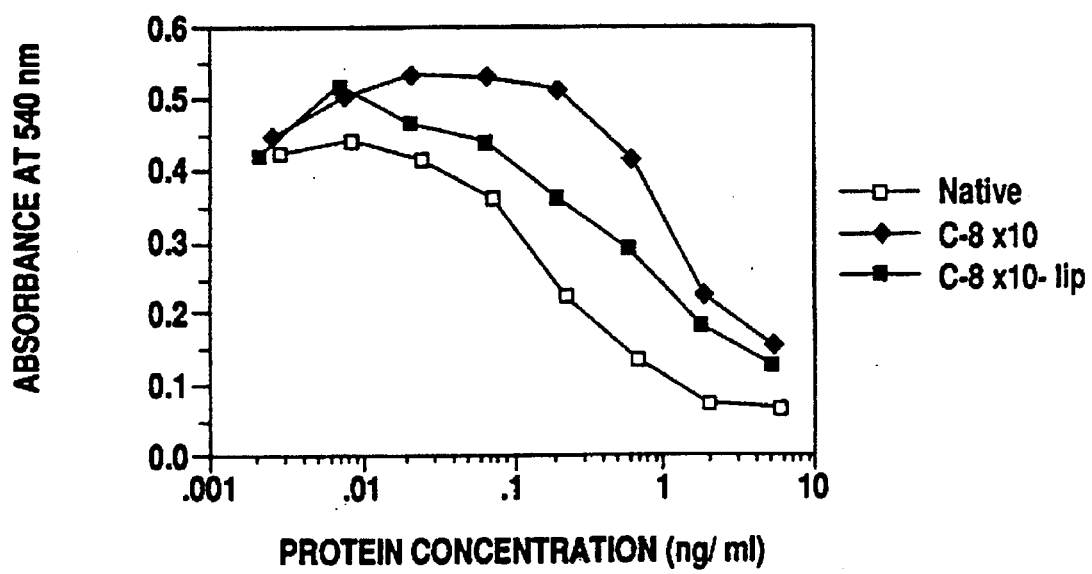

FIG. 15 Cell killing activity of C8 (X5)-TNF-liposomes; C8 (X5), C8 (X10), C8(X10), C8(10), liposomes, C8(X5) liposomes, and native TNF using the L929 target cell (absorbance at 540 nm us protein concentration (ng/ml)).

Figure 16:
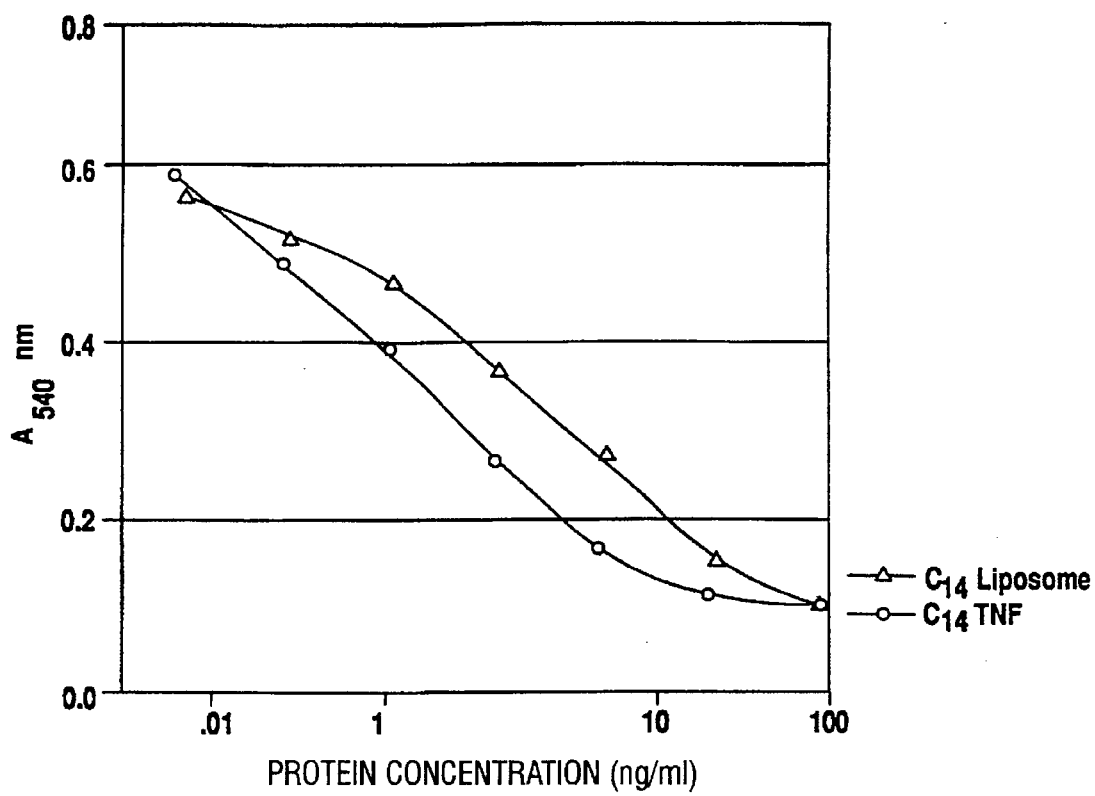
Figure 17:
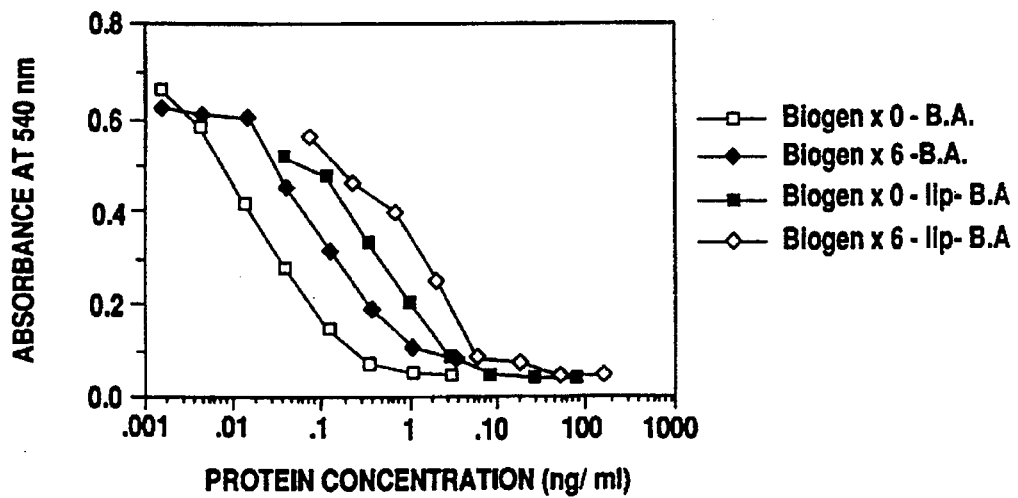

FIG. 16 Biological assay of $C_{14}$ TNF and $C_{14}$ TNF-SUVs using the L929 target FIG. 17 Cell killing activity of $C^8$-Biogen-DSPC liposomal TNF.=Biogen×O-liposomes ▲=Biogen×6-liposomes ■=Biogen×O-liposomes ●=Biogen×6-liposomes.

DETAILED DESCRIPTION OF THE PREFERRED EMBODIMENTS

Applicants have prepared modified TNF molecules with retained cytolytic activity. These modified TNF molecules may also demonstrate increased hydrophobicity by virtue of the selective substitution of TNF amino groups with fatty acid side-chains.

Fatty acid side chains may be associated with TNF at amino residues by a variety of methods. For example a nucleophilic substitution reaction with an N-hydroxysuccinimide ester of a fatty acid, or the use of a fatty acid anhydride method, or the use of a fatty acid chloride method, or the use of a carbodiimide coupling method may be used to facilitate the attachment of a fatty acid to TNF amino residues. Most preferably, the attachment or association of fatty acids to amino residues of the TNF molecule is accomplished through the use of N-hydroxysuccinimide esters of the fatty acid of choice.

N-hydroxysuccinimide esters of fatty acids having carbon chains ranging in length from about 8 to 14 carbon molecules were successfully reacted with rHuTNF to form lipophilic TNF having essentially fully retained biological (cytolytic) activity, as compared to native TNF. Modification with esters of $C_8$ to $C_{14}$ acids occurred as determined by consumption of positively-charged amino groups. Curiously, however, esters of longer chain lengths ($C_{16}$, $C_{18}$) were much less capable of introducing these chains via amide linkages.

Biological assays revealed that retention of activity (i.e., cytolytic activity) was dependent both on the number of fatty acid chains introduced and the chain length of the fatty acid. Biological activity (i.e. tumor cell cytolytic action) was most conserved (>50%) in a TNF preparation modified with ~1–2.5 caprylic acid ($C_8$) residues per TNF trimer.

The claimed TNF preparations were found to bind with liposome surfaces with surprisingly and unexpectedly enhanced efficiency. For example, an enhanced binding efficiency of ~50% was demonstrated by the described lipophilic TNF with the surfaces of preformed DPPC-SUVs. Binding to liposomes was even more efficient (80–90%) for TNF modified with either about 3.5 caprylic acid ($C_8$) residues per trimer or with about 1.5 residues of myristic acid ($C_{14}$) residues per trimer. The biological activity of DPPC-SUV-$C_8$-TNF was found to be comparable to the non-liposomal $C_8$-TNF. Thus, the present invention provides a highly efficient method for preparing the claimed biologically active liposomal-lipophilic TNF compositions with essentially fully retained biological activity.

The marked susceptibility of the biological activity of rHuTNF to the chemical introduction of hydrophobic fatty acid side chains, both with respect to number and length of the fatty acid chain, was an unexpected and important consideration in developing the modified TNF forms of the present invention. Amino functions are required for biological activity of TNF, and only a limited extent of modification is well tolerated. Proteins with enhanced hydrophobicity due to acylation remain capable of interacting with other macromolecules; for example, lysozyme may be monoacylated with fatty acid chains from $C_8$ to $C_{14}$ and thereby demonstrate affinity for PS/DPPC vesicles, and could also be effectively phosphorylated by bound protein kinase C. In contrast, acylation of TNF with particularly long chain fatty acids (16 carbon atoms or greater in length), even at low levels (about 1–2 residues per timer) is demonstrated herein by the inventors to result in marked perturbation of cytolytic activity (FIG. 8). As used herein the term long chain fatty acid is defined as a fatty acid having a carbon chain length of between 8–14 carbons, inclusive.

The possible mechanisms which may precipitate these results are not known at this time. Particular aspects of the unique formulation of liposomes, presenting modified TNF on their outer surfaces, is hypothesized by the inventors to better mimic the mode of delivery employed in vivo by activated monocytes/macrophages demonstrated in tumoricidal reactions in vitro.[42-46] However, it is equally as likely that the modified TNF associates with liposomes as encapsulated within the liposome. Either surface- associated or encapsulated lipophilic TNF may provide the superior in vivo delivery system of the present invention. The claimed TNF preparations are submitted to provide a superior TNF therapeutic agent having enhanced pharmacological acceptability (i.e., having reduced host toxicity).

The inventors have demonstrated that it is possible to prepare with high efficiency a biologically active liposomal associated, modified TNF formulation starting from the parental TNF. The described modified forms of TNF association with SUVs or MLVs provide an improved drug delivery system whereby the toxic side effects associated with TNF may be minimized and/or eliminated.

Most particularly, the amino residues of the TNF molecule focused for the described chemical modification include the basic amino acid lysine (Lys) residues of the TNF amino acid sequence, or of any amino acid which occupies the N-terminal site of the TNF. In its native form, TNF is occupied by a valine amino acid residue at its N-terminus. However, mutated forms of TNF wherein the N-terminus is occupied by other than a valine amino acid are also included among those TNF molecular sites focused for the preparation of the claimed modified TNF. The modified TNF amino residue sites may then include a chemical group which will enhance the hydrophobicity of the TNF molecule. Most preferably, the chemical group comprises a fatty acid having a carbon chain length of between 8–14 carbons, inclusively.

Any variety of chemical processes well known to those of skill in the art may be used to provide the initial reactive sites at the focused amino acid residues of the TNF molecule. The chemical approach most preferred by the inventors for the preparation of modified amino acid residues on TNF is via nucleophilic attack using N-hydroxysuccinimide esters of fatty acids. This approach has been successfully employed by the inventors to create the claimed modified TNF, wherein the modified TNF includes the attachment of fatty acids at the modified amino residues of the TNF.

The most preferred form of TNF is a recombinant human TNF peptide (rHuTNF) modified at less than 5 amino residues per TNF trimer to include a fatty acid, wherein the modified rHuTNF retains its cytolytic activity. Even more preferably, TNF, particularly rHuTNF, is modified at between about 1–3 residues (mole/mole) of $C_8$, $C_{10}$, or $C_{14}$ alkyl chains. Fatty acid modified forms of TNF are then associated with a liposome, most particularly defined as a SUV or MLV.

The SUV most preferably comprises about 4500 molecules of a neutral lipid. More particularly, the neutral lipid is a phospholipid. By way of example, the phospholipid of the SUVs and MLVs may be dipalmitoyl phosphatidylcholine (DPPC) or distearoylphosphatidylcholine (DSPC). SUVs comprised of DPPC are particularly preferred for use in the present invention.

However, the liposomes, and particularly the SUVs described in the present invention, may be comprised of any variety of lipids, especially neutral lipids, capable of associating with the described modified forms of TNF with the enhanced binding efficiency of the claimed invention.

In this regard, other SUV and MLV formulations (i.e., different lipids) and higher liposome-TNF ratios demonstrating an enhancement in binding efficiency of at least about 50% are included within the scope of the preparations disclosed and claimed herein. Assuming a trimeric structure for TNF,[25,47] the SUV-lipid-TNF formulation has an average of about 0.5 moles TNF per mole SUV. However, higher molar ratios of TNF per mole of the liposome preparation may be employed to achieve the essentially 100% binding efficiency of lipophilic TNF to liposome.

An SUV-TNF or MLV-TNF preparation, such as the inventors formulations, may be suitable for enhancing delivery of TNF to the tumor. An SUV-TNF preparation avoids rapid capture by RES, and provides a vectorial display of the TNF toxin on the exterior liposomal surface. Alternatively, MLV-TNF formulations may be preferred where RES-mediated trafficking would facilitate enhanced delivery of TNF to the tumor.

It will be of considerable importance to compare the pharmacokinetics characteristics of the described TNF preparations to that of the native TNF-MLV preparations previously described by Debs et al.[6] Pharmacokinetics models have been employed by the inventors to postulate lower systemic drug levels using a drug-carrier formulation, thereby potentially reducing the TNF related host toxicity of prior described TNF preparations.

The inventors' studies of liposomal-associated lipophilic TNF formulations have demonstrated potent tumor cytotoxicity in vitro. These observations are submitted to provide a reduction in tissue damage and better liver and lung targeting activity in vivo by these preparations compared to free TNF.

A rHuTNF was obtained from Biogen Corporation (Cambridge, Mass.). The fatty acids, N-hydroxysuccinimide, dicyclohexylcarbodimide, the N-hydroxysuccinimide ester of acetic acid and dimethyl sulfoxide (DMSO) were purchased from Sigma Chemical Co. (St. Louis, Mo.). IODO-GEN was obtained from Pierce Chemical Co. (Rockford, Ill.). PD-10 column were obtained from Pharmacia LKB Biotechnology Inc. (Pascataway, N.J.). Carrier-free $Na^{125}I$ was purchased from Amersham Corporation (Arlington Heights, Ill.). L-929 cells were obtained from American Type Culture Collection (Rockville, Md.).

Methods

Since lysyl ε-amino groups are usually in a hydrophilic environment and amenable to chemical modification, the inventors undertook an assessment of the role of chemically reactive amino functions in rHuTNF in the expression of its biological activity.

The data presented herein shows that amino functions in rHuTNF are important for the expression of its biological activity. Only a low level of modification (less than 5 residues per monomer) was tolerated with essentially complete retention of biological activity.

The N-terminal valine is known to be highly mobile by x-ray crystallography,[25] and should therefore be in a hydrophilic environment. Similarly, of the six lysyl residues, two are believed to participate in intra- and inter-subunit ionic interactions, leaving four amino residues as reactive candidates. Chemically reactive amino functions were most preferably modified with the N-hydroxysuccinimide ester of acetic acid. The modification of amino groups to amide, and the concomitant loss of charge, was monitored by native PAGE.

When rHuTNF was reacted with the active ester at increasing mole ratios, up to 12 amino groups per trimer could be modified. When the biological activity of acetylated rHuTNF was determined, a strong correlation between the extent of modification and loss of biological activity was observed. One to three amino groups per trimer could be modified with nearly complete retention (~80–95%) of biological activity; activity was completely destroyed at the highest levels of modification (12 amino residues per trimer). These results reveal important functions for the amino groups of rHuTNF and significant constraints on strategies involving their modification in the development of second-generation-TNF variants.

The fact that the acetylation reaction appeared to plateau at 12 residues, and not 15, suggests that one additional amino group per monomer did not react. Whether this is due, for example, to inaccessibility of one of the lysyl residues in the quaternary structure of the trimer or to hyporeactivity of an amino group with too low a pK may be determined by one of ordinary skill in the art employing the studies proposed herein.

The following Examples 1–9 are presented only to describe the preferred embodiments and utilities of the present invention, and are not meant to limit the scope of the present invention unless specifically indicated otherwise in the claims appended hereto.

EXAMPLE 1—Radioiodination of TNF
EXAMPLE 2—Preparation of Acylated TNF
EXAMPLE 3—Preparation of Lipid Small Unilamellar Vesicles (SUVs)
EXAMPLE 4—Binding of Acylated TNF to Small Unilamellar Vesicles
EXAMPLE 5—In Vitro Cytolytic Activity of Amino-Residue Modified TNF
EXAMPLE 6—In Vitro Cytolytic Activity of Lipophilic Modified TNF
EXAMPLE 7—In Vitro Cytolytic Activity of Liposome-Lipophilic TNF
EXAMPLE 8—Proposed Pre Clinical Development of Pharmaceutically Acceptable TNF Preparations for Human Use
EXAMPLE 9—Proposed In Vivo Use of Liposomal-Lipophilic TNF in Humans

EXAMPLE 1

Radioiodination of TNF

Purified rHuTNF was labeled with $^{125}I$ using the Iodogen procedure as follows: 10 µg of rHuTNF in 40 µl of 1M potassium-phosphate buffer, pH 7.0 was layered over a freshly prepared film of IODO-GEN (10 µg) and incubated for 10 min at 4° C. in the presence of 1 mCi of carrier-free $Na^{125}I$. The reaction mixture was brought up to 0.5 ml volume with phosphate buffered saline (PBS) containing 0.1% gelatin and the unreacted iodine was removed by gel filtration on a Sephadex G-25 PD10 column equilibrated with PBS containing 0.1% gelatin. The column was washed with 2 ml of the same buffer and the flow-through volume was discarded. Radioiodinated TNF was eluted with the next 1.2 ml of the buffer. More than 95% of $^{125}I$-iodine was incorporated into the protein as determined by: (1). trichloracetic acid precipitation of total radioactivity; and (2). SDS-PAGE gel electrophoresis in which a single band of TNF at 17 kDa was detected as radiolabeled. The specific radioactivity of the product was ~55 µCi/µg TNF.

EXAMPLE 2

Preparation of Acetylated TNF

The present example is provided to describe the method by which acetylated TNF was prepared for both the amino acid residue accessibility studies and for the cytolytic activity TNF studies. Having obtained the optimal number of amino residue modification tolerated with retained cytolytic activity, the inventors prepared amino residue modified TNF which included fatty acids of various chain lengths.

a. Preparation of Acetylated TNF for Accessibility of Amino Acid Residues and for Cytolytic Studies of Acetylated TNF Studies Acetylated TNF was prepared using rHuTNF and the N-hydroxysuccinimide esters of acetic acid. The reaction medium contained, in a final volume of 100 µl, 0.1 sodium bicarbonate, various concentration of the N-hydroxysuccinimide ester of acetic acid, 20 µg of cold rHuTNF and $5 \times 10^5$ cpm of $^{125}I$-rHuTNF. The reaction was started by adding various concentrations of the active ester dissolved in 10 µl of DMSO. After incubation at about 26° C. (room temperature) for the indicated times (most preferably, about 3 hours) with gentle stirring, the reaction was stopped by adding excess amount of L-lysine. The reaction mixture was then applied to a Sephadex G-25 column (0.7×5 cm) previously equilibrated with PBS to remove residual active esters, N-hydroxysuccinimide and DMSO. Acylated TNF was fractionated by elution with the same buffer and the radioactive fraction was used as the acylated TNF preparation.

Figure 1A:
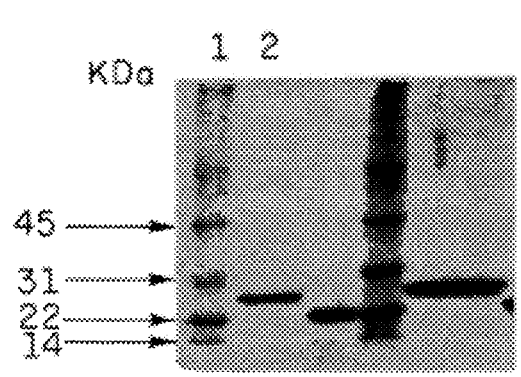
FIG. 1 SDS-PAGE and native-PAGE profiles of rHuTNFC were analyzed by SDS-PAGE (12%) polyacrylamide gel) and by native-PAGE (4%-12% linear gradient gel).
Figure 1B:
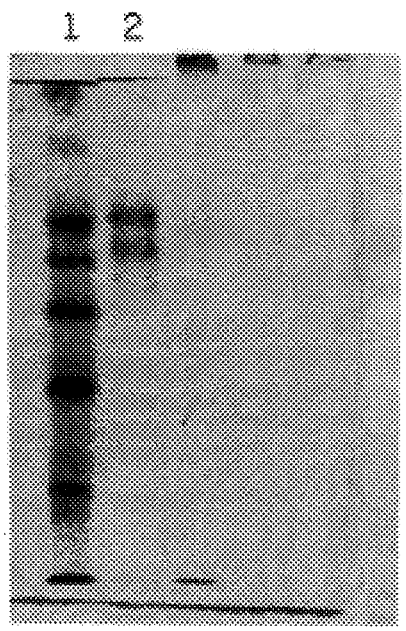

The rHuTNF used in these studies show a single band in SDS-PAGE (12%), whereas it shows two major and one minor bands in native PAGE (FIG. 1). rHuTNF preparations obtained from several other sources also show similar patterns in native PAGE (data not shown). The following flow chart outlines the procedure followed for the C2-acylation of TNF:

C2-acylation of TNF

90 µl of TNF (20 µg cold + 5 × 10$^5$ cpm)
10µl of C2-Osu in DMSO
↓
stirred at room temp. for 3 hr.
↓
15 µl of L-Lysine were added
↓
took into eppendorf tube ——→ count
12,000 rpm, 5 min.

-continued
C2-acylation of TNF

```
            ┌──────────────┴──────────────┐
         pellet                          sup
            │              ┌──────────────┼──────────────┐
            ▼              ▼              ▼              ▼
          count         10 μl          10 μl          the rest
            │              │              │              │
            ▼              ▼              ▼              ▼
        SDS-PAGE         count          count          count
            │              │              │              │
            ▼              ▼              ▼              ▼
         Autrad.        Bioassay       SDS-PAGE       Native PAGE
                                          │              │
                                          ▼              ▼
                                       Autrad       cut Autrad.
                                                         │
                                                         ▼
                                                       Count
``` b. Quantitation of Modified Residues

The extent of TNF modification was determined by measuring the mobility of the modified proteins on native PAGE. 20 μl of the acylation reaction mixture was applied to lanes of a 4%–12% linear gradient polyacrylamide gel, the pll 8.29, and subjected to native PAGE. After silver staining, each protein band was individually cut from the gel and the radioactivity was measured with a gamma counter. A weighted average of modified residues for each preparation was calculated from the counts in these protein bands. As demonstrated in FIG. 5, TNF forms modified with 12 C2 groups had lost virtually all biological activity.

EXAMPLE 3

Preparation of Lipid—Small Unilamellar Vesicles (SUVs)

The purpose of this study was to demonstrate a protocol for the successful preparation of liposomes, most particularly, liposomes having a sufficiently small diameter so as to preclude capture by RES. These small liposomes are called small unilamellar vesicles, and are referred to by the acronym SUV(s). The particular SUV's of the present study had a diameter of between about 0.02–0.05 μm.
Preparation of lipid-small unilamellar vesicles (SUVs).

While any neutral lipid capable of providing the described small vesicle size may be used in the preparation of the formulation of TNF described herein, those lipids most particularly preferred include neutral lipids, and even more preferably the phospholipids. Both saturated and unsaturated phospholipids are contemplated as useful for the described purpose of preparing liposomes. Among the phospholipids, those most particularly preferred include DPPC and DSPC.

In the following study, small unilamellar vesicles (SUVs) were prepared from the phospholipid DPPC. 10 mg of DPPC was first dissolved in a small volume of chloroform and the solvent was dried under vacuum in a glass test tube. After addition of I ml of PBS (pH 7.4), the dried DPPC was hydrated with repeated vortexed mixing at 50° C. for 30 min. The suspension was sonicated at 50° C. for 30 min. using a probe type sonicator (Heat System; Farmingdale, N.Y.) and then centrifuged at 1500 xg for 10 min. to remove titanium particles.

Binding of TNF to DPPC-vesicles was determined by gel filtration as described in Example 4.

EXAMPLE 4

Binding of Acylated TNF to Small Unilamellar Vesicles (SUV's)

The following example is presented to demonstrate the enhanced binding efficiency of modified tumor necrosis factor molecule to the surface of liposomes, most particularly those small liposomes described as small unilamellar vesicles (SUVs).

The present experiment was also performed in order to determine whether acylated forms of TNF had binding affinity for liposomal surfaces. The present study also demonstrates the highly efficient method of providing liposome-associated TNF forms developed by Applicants. High levels of binding efficiency are provided for both the association of modified TNF to SUV's and the encapsulation of modified TNF by MLV's.

In these studies, the inventors were successful in developing a liposomal associated-acylated TNF delivery system having an essentially 100% binding efficiency. These results demonstrate a significant enhancement over prior TNF delivery systems. Additionally this enhanced binding efficiency represents a significant advancement over prior methods, wherein an only 2–11% MLV encapsulation efficiency is reported with unmodified forms of TNF. As used herein, the term unmodified TNF is defined as a TNF molecule whose N-terminal amino residue or lysine amino residues have not been chemically altered so as to include or facilitate the attachment of chemical groups which would increase the hydrophobicity of the TNF molecule. More specifically, chemical groups which would increase the hydrophobicity of the TNF molecule include, by way of example, fatty acids.

For these studies, the SUV formulations of modified TNF covalently linked to alkyl side chains of various lengths as described and prepared in Example 2 were employed.

The most preferred example of the described SUV associated modified TNF molecules is the TNF molecule modified with about 1–2.5 residues of caprylic ($C_8$) fatty acid chains per TNF trimer. This particular modified TNF molecule was exposed to preformed SUVs comprised of either DPPC phospholipid or DSPC phospholipid. The results in this example demonstrate that, whereas native TNF showed only a negligible propensity for association, a high degree (50–95%) of association was observed for the lipid-modified TNF. This observation correlated with extent of lipid substitution of the TNF and with the chain length of the lipid comprising the SUV.

In the present studies both native TNF and acetylated TNF bound liposomes with poor efficiency (FIG. 9, <5% binding efficiency). These studies also demonstrated that DPPC and DSPC-SUV-lipid-TNF formulations had temperature stability profiles. Although their stabilities were similar at room temperature, elevation of the temperature to 37° C. revealed the instability of the DPPC-$C_8$-TNF from the void volume. The phase-transition temperature of DPPC in SUVs is 37° C., which is the likely cause for the instability. In contrast, the DSPC-$C_8$-TNF remained largely intact at this temperature; the phase-transition temperature of DSPC in SUVs is 55° C.

Additionally, as is demonstrated in the following cytolytic assays with TNF, when the lipid-TNF was presented in DPPC-SUVs, the biological activity was retained or even enhanced slightly compared to free lipid-TNF (FIG. 13). In contrast, DSPC-SUVs appeared to be poor carriers of lipid-TNF, as biological activity was reduced (FIG. 17). The reason for this is unclear but is postulated to be due to several factors, including SUV-mediated reduction in TNF-receptor-ligand collision frequency, or other perturbations of receptor-ligand interactions attributable to the relative rigidity of the DSPC-SUV.

These data also show that, while the DPPC preparation demonstrated a reversible association with the $C_8$-TNF at 37° C., the DSPC preparation was significantly and highly more stable under these same conditions. However, both TNF and SUV formulations prepared with either of the described phospholipids displayed cytotoxic activity in vitro. These data demonstrate Applicants' highly efficient preparation of stable, cytologically active liposomal-TNF formulations.

Binding to DPPC Vesicles The affinity of acylated TNF's for DPPC-vesicles was determined by binding of $^{125}$I-native, $^{125}$I-$C_2$-, $^{125}$I-$C_8$- and $^{125}$I-$C_{14}$-TNF to DPPC-SUVs and quantitated by partioning using Sephadex G-200 column chromatography. More specifically, $^{125}$I-native or $^{125}$I-acylated TNF (5 μg, 5×10$^4$ cpm) ($^{125}$I$C_8$-TNF, $^{125}$C$_{14}$-TNF, etc) were individually mixed with 500 μg of DPPC-vesicles, respectively, and incubated at 20° C. for 15 min. The incubation mixture was applied to a Sephadex G-200 column (1×15 cm) previously equilibrated with PBS and vesicle-bound and unbound proteins were fractionated by elution with the same buffer. The radioactivity in each fraction (0.5 ml portions) was measured by gamma-counting.

$^{125}$I-TNF was prepared as described in Example 1. The procedure employed in binding acylated TNF to liposomes is summarized in the following chart:

Binding of Acylated TNF to DPPC-Liposomes

500 μg of DPPC-SUV in PBS
5 μg of acylated TNF (5 × 10$^4$ cpm)

↓ incubated at room temperature for 15 min.

↓ applied to Sephadex G-200 column (7.0 ml)
previously equilibrated with PBS

↓

0.5 ml portions were collected

↓

Count

Typical profiles of the separation of $^{126}$I-TNF-DPPC vesicle complexes from unbound protein are shown in FIG. 9. DPPC vesicles or protein-DPPC-vesicles complexes were eluted in the void volume fraction as indicated by arrows.

Figure 9A:
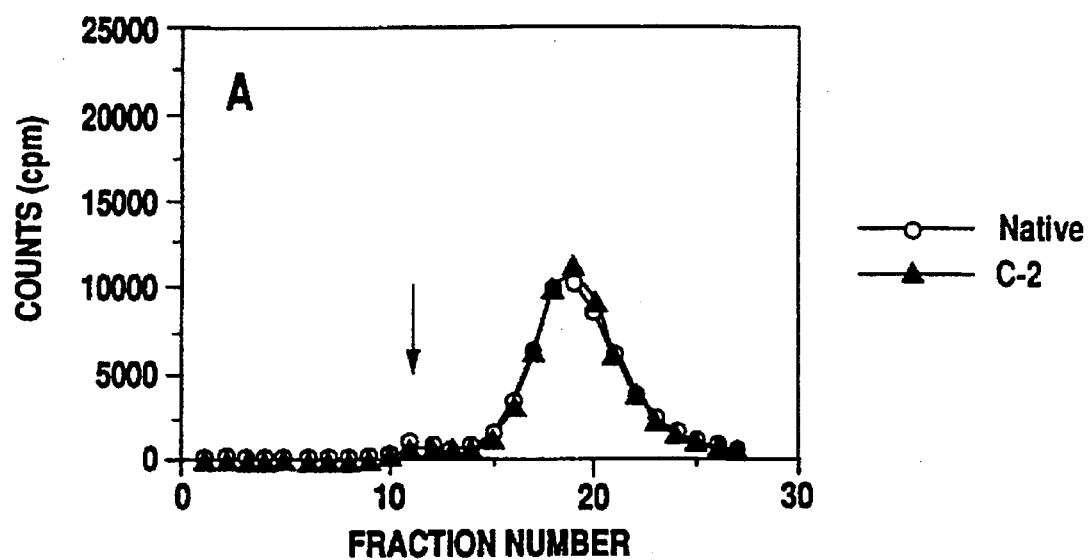
Figure 9B:
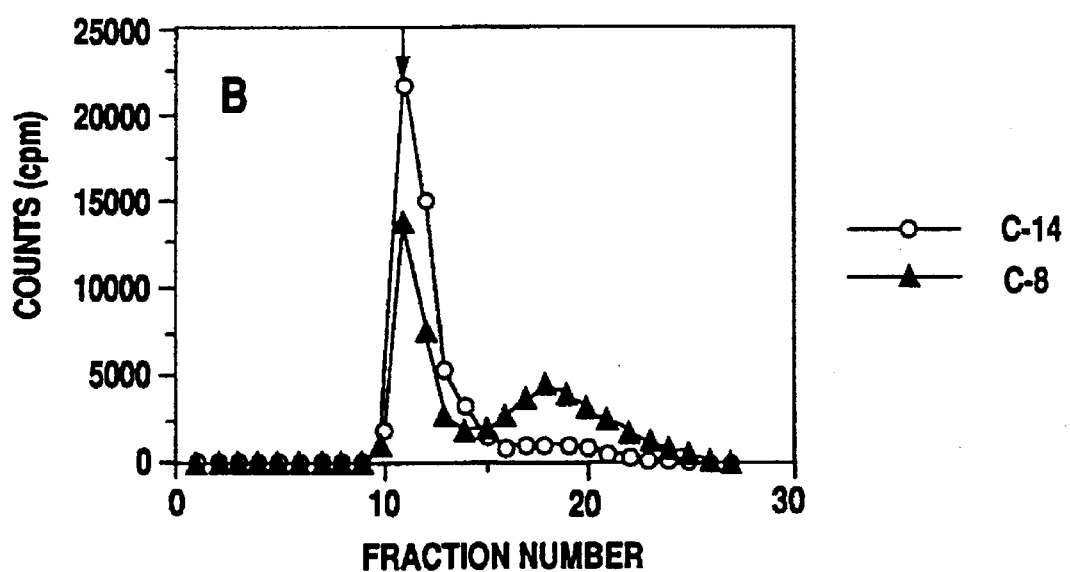

As shown in FIG. 9a, binding of $^{125}$I-native TNF to DPPC-vesicles was negligible. $C_2$-TNF modified to contain two fatty acid groups per trimer scarcely bound to the vesicles, as shown in FIG. 9A. With $C_8$-TNF having the same level of modification, more than 85% of the added protein was found to be bound to the vesicles (FIG. 9b).

FIG. 10 shows the effect of the number of modified residues on the binding of $C_2$- and $C_8$-TNF to DPPC-SUVs. $C_2$-acetylation of TNF did not cause a detectable increase in the binding of TNF to DPPC-vesicles, even when 6 residues per trimer were modified. In contrast, binding of $C_8$-TNF increased significantly as the number of modified residues increased, and more than 80% of added TNF was bound to vesicles when the number of modified residues exceeded 3.5 residues per trimer.

EXAMPLE 5

In Vitro TNF Cytolytic Activity of Residue Modified TNF With and Without Various Fatty Acids The following in vitro assays were performed to (1) assess the role of chemically reactive amino functions in rHuTNF in the expression of TNF biological activity (Example 5), and, obtaining data establishing that low levels of TNF molecule amino residue modification (1–3 residues per trimer) can be made without a significant loss in biological activity, to (2) assess the biological activity of lipophilic forms of low-level amino residue acylated TNF with long chain fatty acids (C8–C18) (Example 6).

The following examples 5 and 6 are also provided in order to establish the applicability of the present invention as an anti-tumorigenic agent in vivo particularly for use in humans as an anti-cancer pharmacologically acceptable preparation.

(a). Preparation of TNF having different levels of modified amino residues.

Acetylated TNF having different levels of modified amino residues were prepared according to the protocol outlined in Example 2, part (a). The particular amino-residue modified acylated TNF forms employed in this study included:

1–2 amino residue modified TNF
3–5 amino residue modified TNF

Figure 2:
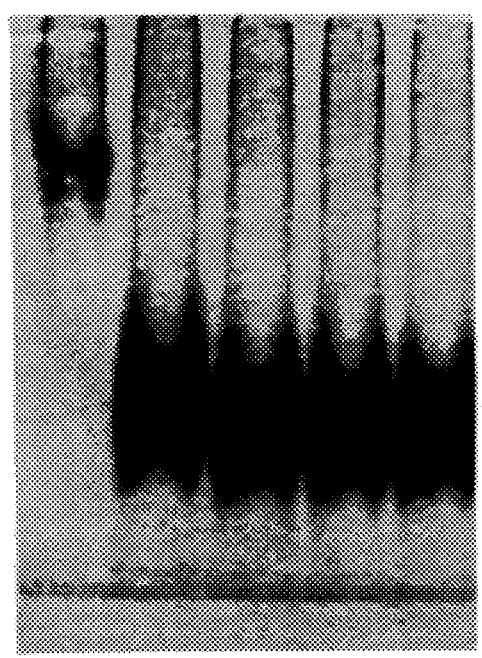
FIG. 2 Time course of acetylation of amino residues of TNF. After the acetylation reaction with 80 times excess amount of active ester at room temperature for the indicated time, the reaction was stopped by adding an excess amount of L-lysine. The reaction mixture was applied to native-PAGE to determine the extend of modification.
Figure 3:
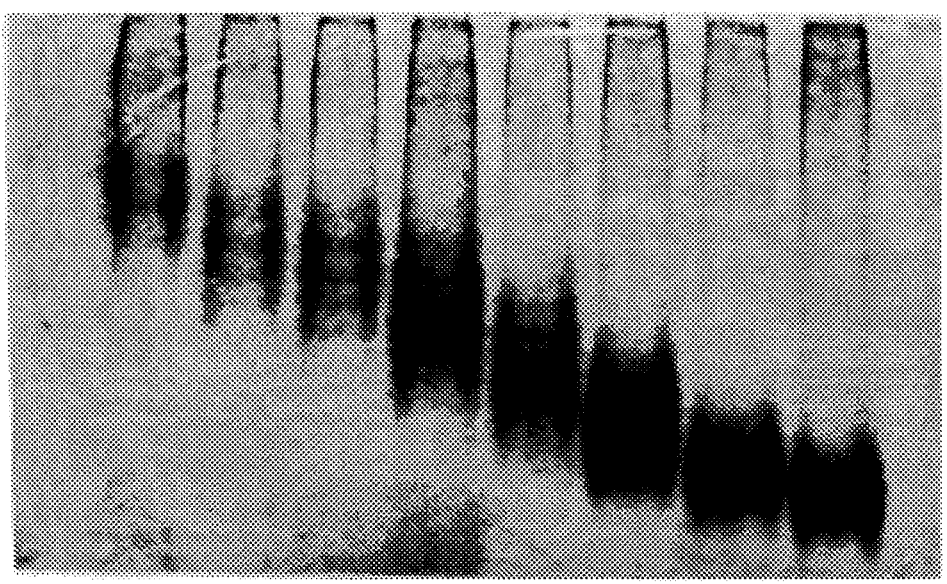
FIG. 3 Effect of molar ratio of $C_2$ active ester/TNF on the extent of acetylation of rHuTNF. rHuTNF was modified with the indicated ratio of active C2 ester/TNF at about 26° C. (room temperature) for about 3 hr and the extent of modification was determined by native-PAGE analysis. rHuTNF preparations were reacted with molar ratios of N-hydroxysuccinimide ester of acetic acid. Greater mobility reflects amidation of charged amino groups.
Figure 4A:
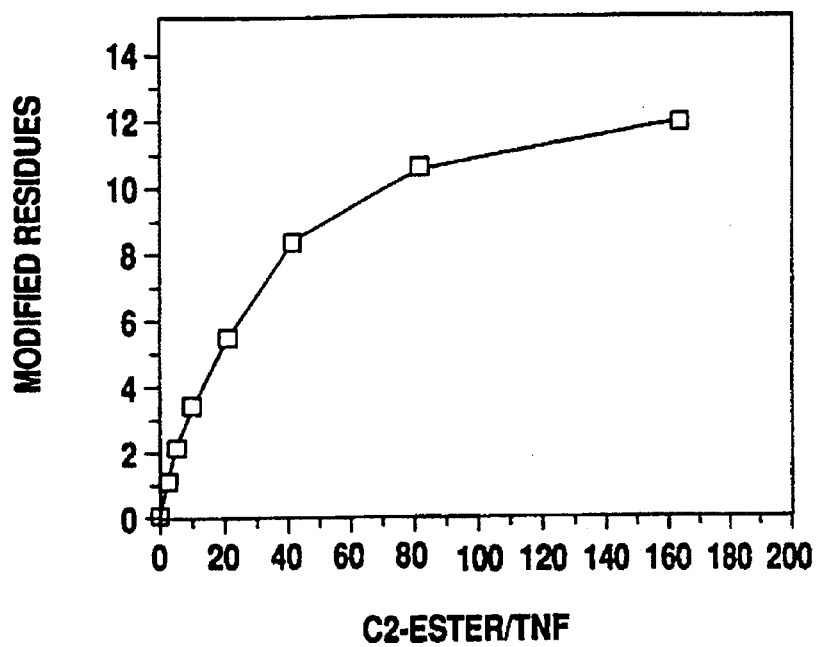
FIG. 4-4(a) Effect of increasing molar ratio of active $C_2$ ester/TNF on the number of average modified amino group residues of acetylated TNF. The number of average modified amino residues were calculated from the radioactivity in each of the protein bands in FIG. 3 and were plotted against the ratio of active ester/TNF.
Figure 4B:
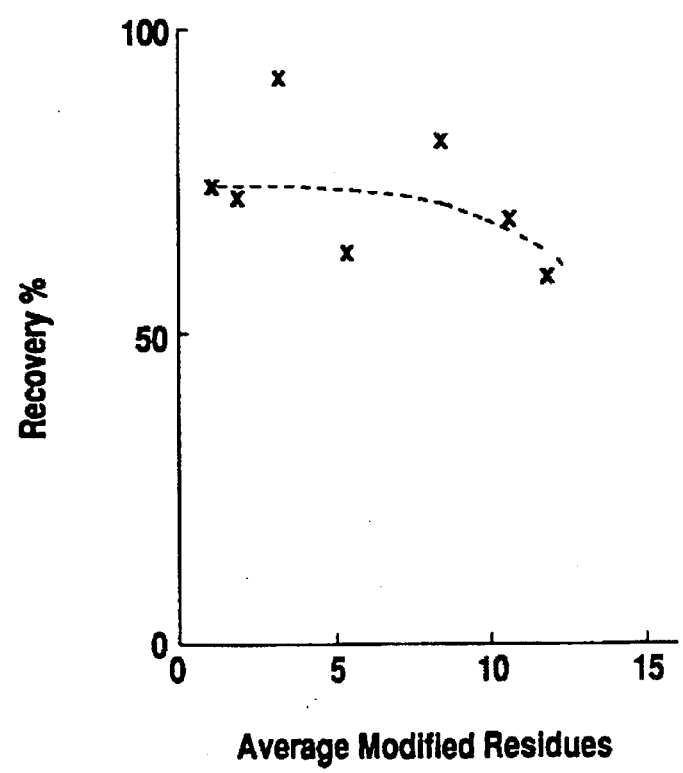

FIG. 2 shows the time course of acetylation of amino residues of TNF, using an 80-fold molar excess of N-hydroxysuccimide ester of acetic acid to protein. Due to a decrease in the number of free amino residues, the mobility of TNF on native PAGE increased as the modification reaction proceeded. The electrophoretic microheterogeneity of TNF was also observed to increase with acylation. The modification occurred rapidly, and was nearly complete after 5 min., reached a plateau by 10 min. After 10 minutes, no further reaction was evident, even after 6 hrs. FIGS. 3 and 4 show the effect that increasing the molar ratio of active-ester/TNF has on the extent of acetylation of TNF after a 3 hr reaction. The extent of modification was highly dependent on the molar ratio of these components active ester to TNF; it increased linearly as the ratio increased, reaching a plateau at 12 amino residues modified per trimer with the highest active ester/TNF ratio employed.

Quantitation of Modified Residues

The extent of modification was determined by measuring the mobility of the modified proteins on native PAGE as described in Example 2. Briefly, 20 μl of the acylation reaction mixture was applied to lanes of a 4%–12% linear gradient polyacrylamide gel, pH 8.29, and subjected to electrophoresis. After silver staining, each protein band was individually cut from the gel and the radioactivity was measured with a gamma counter. A weighted average of modified residues for each preparation was calculated from the counts in these protein bands FIG. 4(b).

(b). Involvement of amino groups of TNF in the expression of cytolytic activity of TNF.

To determine the involvement of amino groups of TNF on the expression of its cytolytic activity, acetylated TNF with different levels of modified residues was subjected to biological assay on actinomycin D-treated L-929 cells.

TNF cytolytic activity was determined as previously described.[48] L929 cells were plated at $15 \times 10^3$ per 150 µl of DME/F12 medium in 0.33 cm$^2$ wells. After an overnight incubation of the variously amino residue modified TNF preparations from part (a), 50 µl of actinomycin D containing medium were added to give a final drug concentration of 1 µg/ml. Samples of acetylated TNF from the procedures described herein (at Example 2) were immediately titered on those targets and incubations continued overnight.

After 18–24 hr, 50 µl of neutral red solution were added and the remaining viable targets were allowed to incorporate dye for 60 min. Unincorporated dye was removed by washing once with PBS.

Incorporated dye was solubilized with acidified ethanol and the $A_{540}$ for each well was determined using a multichannel scanning apparatus. $LD_{50}$ of each sample was obtained from the titration curve of $A_{540}$ and TNF dose and the relative cytolytic activity (%) was calculated by comparing the $LD_{50}$ of the sample with that of native TNF.

FIG. 5 shows the dose response curves for the cytotoxic activity. The relative cytotoxic activity of acetylated TNF sample compared to native TNF was calculated from the $LD_{50}$ values and plotted against the number of modified residues (FIG. 6).

Results:

More than 90% of the cytotoxic activity was retained when 1–2 amino residues per TNF trimer were modified. However, substitution of TNF to the level of 3–5 residues per trimer caused 30% to 70% loss of activity. Maximum modification (~12 amino residues per trimer) caused more than 95% loss of activity.

The results from this experiment demonstrate that the loss of biological activity of TNF closely paralleled the extent of modification of the lysine amino groups of the TNF. In these studies, it was also established that TNF molecules modified at less than 5 lysine amino residues per TNF trimer had retained cytolytic activity. Most preferably, it was established that TNF preparations wherein between about 1–3 lysine amino residues per TNF trimer were modified retained the greatest degree of cytolytic activity.

EXAMPLE 6

In Vitro Cytolytic Activity of Fatty Acid Modified TNF

The present experiment was performed in order to determine if amino-residue modified TNF which were further modified to include fatty acid chains, (at the modified amino residues) particularly long chain fatty acids, had retained cytolytic biological activity. The term long chain fatty acid is defined as a fatty acid having a carbon chain length of between 8–14 carbons.

The discovery that low levels (less than 5 residues, most preferably between about 1–3 residues per trimer) of amino modification are well-tolerated in TNF obtained from the results in Example 5, presented the inventors the opportunity for expanding the scope of application for the potential use of this agent in treating humans. For example, in rHuIl-2, introduction of polyethylene glycol adducts via lysyl or cysteine modification has been shown to preserve biological activity and increase the half-life of the molecule in vivo.[14-17] The chemical modifications of TNF described herein are also postulated to advantageously attenuate the immunogenicity of this molecule.[18,19] Thus, Applicants' specifically defined strategies of chemical modification of TNF will be useful in overcoming the toxic dose limitations of using TNF evidenced in prior in vivo trials.[34-37]

Preparation of Lipophilic TNF

In this example, the inventors acylated amino residues of TNF to low levels with long chain fatty acids ($C_8$–$C_{18}$) to synthesize the lipophilic TNF, and tested the cytolytic activity of these formulations in vitro. Acylated TNF-liposomal lipophilic TNF were prepared for this study by essentially the same procedure described in Experiment 2.

The modification of reactive amino residues on TNF molecule may be accomplished with a variety of methods well known to those of skill in the art. By way of example, the modification of TNF so as to facilitate the introduction of fatty acid side chains, thereto include (1) the modification of amino groups to an amide using N-hydroxysuccinimide esters of fatty acids; or (2) by using a fatty acid anhydride method; or (3) by using a fatty acid chloride method; or (4) by using a water-soluble carbodiimides method.

Fatty acid anhydrides and chlorides are commercially available or can be readily synthesized. These can be reacted directly with the protein, and will be attacked by amino functions, thereby introducing fatty acid side chains through amide linkages. Carbodiimides are reacted first with the free fatty acid to activate the carboxyl function; this activated carboxyl function will also be susceptible to attack by protein amino functions. However, the most preferred method to be used to modify the TNF amino residues so as to facilitate the introduction of fatty acid side chains to the TNF is through the use of N-hydroxysuccinimide esters of the fatty acid. More specifically, acylated TNF was prepared using rHuTNF and the N-hydroxysuccinimide esters of fatty acids.

The esters were synthesized by the method of Lapidot et al.[49] The reaction medium contained, in a final volume of 100 µl, 0.1M sodium bicarbonate, various concentrations of the active ester of a particular fatty acid, 20 µg of cold rHuTNF and $2\times10^5$ cpm of $^{125}$I-rHuTNF. The reaction was started by adding various concentrations of the active ester dissolved in 10 µl of DMSO. After incubation at about 26° C. (room temperature) for about 3 hrs with gentle stirring, the reaction mixture was applied to a Sephadex G-25 column (0.7–5 cm) previously equilibrated with PBS to remove residual esters, N-hydroxysuccinimide, and DMSO. Acylated TNF was fractionated by elution with the same buffer and the radioactive fraction was used as the acylated TNF preparation. The quantition of modified residues was performed essentially as described in Example 2. A weighted average of modified residues for each preparation was calculated from the counts in the obtained protein bands.

FIG. 7 shows the effect of fatty acid chain length on the extent of acylation of TNF amino residues by the respective activated esters. In this case, TNF was modified by using a limited amount (5- and 10-fold molar excess) of active esters of each fatty acid to obtain a low level of modification.

Approximately equivalent extents of modification occurred with fatty acids from $C_8$ to $C_{14}$ in length (about 1–2 residues per trimer), whereas the extent of modification decreased as the fatty acid chain length increased beyond this. No significant fatty acid modification of the TNF molecule was observed with $C_{18}$. Therefore, acylated TNFs with fatty acid chain lengths from $C_2$–$C_{14}$ were used in the next series of experiments. Specifically, the tested species of fatty-acid modified TNF included TNF represented in the following list:

C-2=C$_2$-TNF
C-8=C$_8$-TNF
C-10=C$_{10}$-TNF
C-12=C$_{12}$-TNF
C-14=C$_{14}$-TNF Cytolytic Activity of Lipophilic TNF For use in the present study, TNF cytolytic activity was determined as previously described. Briefly, L929 cells were plated at 15×10$^3$ per 150 μl of DMF/F12 medium in 0.33 0m$^2$ wells. After overnight incubation, 50 μl of actinomycin D containing medium were added to give a final drug concentration of 1 μl/ml. Samples of native or acylated TNF or their liposomal formulations were immediately tittered on these targets and incubations continued overnight.

After 18–24 hr., 50 μl of neutral red solution was added and the remaining vaible targets were allowed to incorporate dye for 60 min. Unincorporated dye was removed by washing once with PBS.

Incorporated dye was solubilized with acidified ethanol and the A$_{540}$ for each well was determined using a multichannel scanning apparatus. LD$_{50}$ of each sample was obtained from the titration curve of A$_{540}$ and TNF dose and the relative cytolytic activity (%) was calculated by comparing the LD$_{50}$ of the sample with that of native TNF.

FIG. 8 shows the offset of fatty acid chain length and number of modified residues on the cytolytic activity of acylated TNF. In the case of acetylated TNF (C$_2$), modification at the level of 1–3 residues per trimer caused only a slight decrease (10–30%) in the cytolytic activity. On the other hand, the same level of modification with longer chain fatty acids caused more significant loss of activity. TNF coupled with 1–2.5 caprylic acid (C$_8$) chains per trimer retained 50% of this cytolytic activity. Thus, in a most preferred embodiment of the claimed modified TNF preparations, the TNF molecule is modified at between 1–3 amino residues to include a fatty acid having a carbon chain length of 8 carbons. Generally, this study demonstrated that the extent of loss of cytolytic activity parallels both the increase in number of modified amino residues and the increase in the chain length of the fatty acid employed.

EXAMPLE 7

In Vitro Cytolytic Activity of Liposome-Lipophilic TNF

The present experiment was performed to determine whether acylated forms of TNF prepared in association with liposomes had retained cytolytic activity in vitro. Also, the present studies were conducted to establish the applicability of employing the acylated liposomal-associated TNF forms in vivo for use in humans as a potential anti-cancer therapeutic agent.

To determine the cytolytic activity of liposome-associated acylated TNF, C8-TNF bound to DPPC-vesicles (as prepared according to Example 4) were first purified by gel filtration to remove unbound proteins and then the cytolytic activity of the complexes in the void volume was tested. Results: FIG. 5 shows the dose-response curves for the cytolytic activity of native, C$_8$- and DPPC-SUV-C$_8$-TNF (Liposome lipophilic TNF). C$_8$-TNF shows slightly decreased cytolytic activity (~60% of native TNF), but otherwise the shape of its dose-response curve was quite similar to that of native TNF. DPPC-SUV C$_8$-TNF demonstrated almost the same LD$_{50}$ as free C$_8$-TNF. However, the profile of the dose-response curve was slightly different from C$_8$-TNF and it showed relatively stronger activity in the low protein concentration range.

EXAMPLE 8

Proposed Pre-Clinical Development of Pharmaceutically Acceptable TNF Preparations for Human Tumor Use rHuTNF evaluated in Phase I/Phase II[34-37] clinical trials worldwide as an anti-cancer agent has revealed disappointing efficacy even with dose regimens which evoke marked toxicities, principally hypotension.

To this date Phase I trials have discouragingly revealed that even partial responses were rarely noted and were transient, even at dose-limiting toxicities, including hypotension and thrombocytopenia.[37] Concomitant with these initial clinical impressions, much has since been learned about the complex physiology of TNF from in vitro and animal studies. Indeed, it is much more than a "tumor necrosis factor"; for example, it is identical to cachectin,[33] the active agent in cachexia, and it causes many of the deleterious effects of endotoxin-induced injury.[38,50,51] In addition, the cellular basis for the hypotension observed in the dog model[38] and in the clinic may be perturbation of endothelial cell (EC) physiology. Knowledge that TNF is capable of causing hemorraghic necrosis of certain transplantable tumors in vivo[32] and capable of direct tumor cytoxicity in vitro[52] has, however, prompted a variety of researchers to seek methods of reducing the oftentimes lethal side effects of TNF.

The inventors' studies have led to the development of new strategies to enhance therapeutic gain and minimize toxicity, including the design of second-generation TNFs with better therapeutic indices and the application of drug targeting systems. The goal of the present proposed study is to develop TNF variants which have greater efficacy and lower toxicity in in vitro model systems and which may be efficiently formulated as stable liposomal preparations.

The specific Aims of the present prophetic example for the pre-clinical evaluation of the claimed formulations include:

a. Development of Second-Generation TNFs
  1. Site-directed mutagenesis of native mature TNF.
  2. Amino-terminal extensions with basic peptides.

Development of Lipophilic Adducts of TNFs, either native mature protein or variant(s) derived in the Aim (a) via:
  1. Chemical acylation with activated esters of fatty acid side chains of lysyl or N-terminal amino groups;
  2. Cell-mediated myristylation by recognition of N-terminal peptide signal encoded by mutant cDNA resulting from fusion of this sequence to TNF cDNA;
  3. Construction of mutant TNF cDNA with amino-terminal extension encoding transmembrane domain.

Preparation of liposomal formulations of lipophilic TNF adducts from Aim b. Both SUV and MLV formulations will be evaluated with respect to effect of lipid composition and charge on efficiency of association and stability.

d. Characterization of Free and Liposomal TNF and Second-Generation TNF Formulations in vitro:
  1. Efficiency
    i. Specific activity
    ii. Spectrum of susceptible targets
  2. Toxicity
    i. Hypotension-Endothelial cell model
    ii. Cachexia Lipoprotein Lipase/lipolysis models a. A Second Generation TNF

The inventors propose that modification of the TNF molecule at the N-terminal amino residue or the lysine amino residues of the molecule will facilitate the association of TNF with liposomes. Increased basicity in the N-terminal region of TNF may enhance TNF antitumor activity with less toxicity. TNF mutants as generated with increased basicity have expressed higher cytotoxicity than parental TNF.[26-29] In the present application the inventors propose to study the effect of basicity in the N-terminal region of TNF on both antitumor activity and toxicity, particularly with the coupling of these modified TNF molecules with liposomes (e.g., SUVs and MLVs) in the proposed systematic manner included herewith. The purpose of this study is to produce second-generation TNFs with mutations in the N-terminal region by site-directed mutagenesis techniques. These particularly modified TNF molecules may then be advantageously coupled with liposomes to provide the claimed pharmacologically acceptable preparations.

Experiments a.1. site directed mutagenesis of TNF.

A general approach to generate random mutations in a predetermined region has been well-established.[53] The inventors propose to use this technique to generate a series of mutations in the region encoding the N-terminal 11 amino acids of TNF where increased basicity enhances cytotoxicity. Briefly, the supercoiled plasmid DNA containing TNF cDNA will be isolated and incubated with a single stranded oligonucleotide corresponding to the first 11 N-terminal amino acid residues of mature TNF. In the presence of recA protein and ATP, the single-stranded fragment will be paired to the complementary sequence on the plasmid circular DNA to form a D-loop. The D-loop region (encoding the first 11 amino acid residues in the mature TNF) can be nicked by treatment with the single-strand- specific endonuclease S1. This way, the relaxed circular DNA molecules will have a nick somewhere in the region encoding the N-terminal 11 amino acid residues. By subsequent treatment with exonuclease II and mutagenesis by sodium bisulfate, a panel of point mutations in this region can be generated and confirmed by DNA sequencing.

An alternative and more specific approach the inventors particularly prefer is to convert nonbasic amino acids in this region into the basic amino acids, Arg or Lys. Among the first 11 amino acid residues, (SEQ. ID NO:1)
N—Val—Arg—Ser—Ser—Ser—Arg—Thr—Pro—Ser—Asp—Lys—C
   1    2  3   4    5    6    7    8   9   10  11 three (2, 6, 11) encode basic amino acids. The inventors propose to use 10 oligonucleotide site-directed mutagenesis to change each non-basic amino acid residue into Arg or Lys. If any single mutation is found to enhance cytotoxicity, the inventors may then further generate double-mutation mutants which convert two non-basic amino acid residues into basic amino acid residues if basicity in the N-terminal region does significantly enhance cytotoxicity. Enhancement of cytotoxicity is proposed to be evaluated by the procedures outlined in Aim d.

Substitution with Lys rather than Arg may be preferable in the described modified TNFs. Lys is most particularly preferred for at least two reasons: 1 ) it provides a target for acylation (aim b); and 2) Lys mutants may avoid some isolation problems encountered with Arg mutants expressed in bacteria due to enhanced DNA binding. The inventors hypothesize a plateau wherein further increases in basicity according to the proposed method (e.g., substitution with Lys or Arg) will not provide a further enhancement of biological activity (cytolysis). This plateau may also be determined in the present study using the described methods.

a.2. Preparation of Amino Terminal Extension with Basic Peptides

When a tetrapeptide Arg-Ile-Arg(SEQ. ID NO: 2)-Met is linked to the N-terminus of TNF, the resulting mutant (termed rTNF-$S_{CW2}$) shows broader and significantly higher cytotoxicity to tumor cells both in vitro and in vivo than native TNF.[26-28] The approach of the extension of TNF with basic peptides in the N-terminal region provides a potentially useful method for producing second-generation TNFs with higher and broader cytotoxicity and lower toxic side effects. The purpose of this study is to generate additional second-generation TNFs by increasing basicity with extended basic peptides in the N-terminal region having enhanced cytotoxicity.

To accomplish the above objective, it is proposed that the tetrapeptide Lys-Ile-Lys-Met be added to the N-terminus of TNF.

The Lys-Ile-Lys-Met (SEQ ID NO: 3) tetrapeptide may also provide a better acceptor site(s) for a chemical acylation with activated esters of fatty acid side chains. In addition to the above described tetrapeptide, it is to be understood that many other different combinations of amino acid residues may be used to generate basic peptides. However, sequences with paired basic residues (Arg-Arg, Lys-Lys, Arg-Lys, Lys-Arg) should be avoided in the tetrapeptide of choice since these are potential target sites for proteolysis in other systems where they flank sequences for mature peptides within propeptides.

These sequences, however, do exist in the TNF leader sequence and are not cleaved, at least until the complete pro-hormone is expressed in the membrane.[44] However, to maximize basicity in a small peptide, the inventors propose to substantially increase the number of Arg and Lys residues and to diminish the use of the acidic amino acid residues, Asp and Glu. Most preferably, a peptide containing Arg or Lys in every two amino acid residues are preferred in the described tetrapeptide.

If increased basicity is the major reason for enhanced cytotoxicity of TNF, the inventors hypothesize that this peptide will also enhance cytotoxicity. In addition to providing a simple way to test the notion that increased basicity in the N-terminal region is the major reason to enhance cytotoxicity, the Lys-Ile-Lys-Met(SEQ ID NO: 3) tetrapeptide may also provide a better acceptor site for chemical acylation with activated esters of fatty acid side chains (Aim b.) which will be useful for development of liposomal TNF (Aim c.).

To further increase basicity in the N-terminal region, it is proposed that longer peptides with Arg or Lys residues may be added to the N-terminal region. As already noted, there are many different combinations of amino acid residues to generate basic peptides. To maximize residue basicity in a small peptide, it is proposed that paired basic amino residues (e.g., Arg and Lys) will be avoided as will acidic amino acid residues, such as Asp and Glu. A peptide containing Arg or Lys in every two amino acid residues would be particularly preferred. For example, the oligonucleotides corresponding to the Arg-Ile-Arg-Met (SEQ ID NO: 2) or Lys-Ile-Lys-Met (SEQ ID NO: 3) can be used as a single unit. When the oligonucleotides are ligated to the cDNA encoding TNF, one monomer will generate one tetrapeptide and the dimer will generate an octapeptide, and so on. In this manner a panel of recombinant TNFs with 4, 8 or 12 extended amino acid residues enriched in Arg and/or Lys in the N-terminal region may be generated.

Although addition of tetrapeptide Arg-Ile-Arg-Met (SEQ ID NO: 2) has been shown to enhance cytotoxicity of TNF, it is not yet clear how long the peptide can be extended to the N-terminus of TNF. Addition of a long peptide (e.g., particularly 12 amino acids or even longer) might create stearic hindrance for interaction between TNF and its receptor or might effect the trimer formation of functional TNF. However, the promising results from the addition of tetrapeptide encourage further extension of basic amino acid residues in the N-terminal region of TNF.

b. Development of Lipophilic Adducts of TNF.

Lipophilic adducts of TNF may be prepared according to many different chemical and biochemical processes. The inventors provide herein at least 3 of those methods which would provide these lipophilic adducts of TNF: (1) chemical acylation with fatty acids; (2) myristylation in situ and (3) amino terminal tagging of TNF with transmembrane sequences in vitro.

b.1. Chemical Acylation with Fatty Acids

The purpose of this study is well advanced as described in Section A. One of the difficulties that has been revealed in these studies is the slight to substantial loss of biological activity incurred upon chemical acylation. This loss occurs apparently through both loss of amino functions directly and through introduction of increasingly hydrophobic substituents. The purpose of this experiment is to develop strategies to overcome this loss in biological activity.

While it is postulated that TNF substituted with hexanoic acid groups ($C_6$) is as capable if not better able, to retain biological activity that TNF modified with caprylic acid ($C_8$), the inventors intend to test this hypothesis in the presently proposed experiment. It has, however, been generally observed that increases in hydrophobicity cause losses of activity. Upon determining if $C_6$-TNF is fully active, the inventors will characterize this preparation with $C_6$ for its liposome-binding ability, as described in Aim c.

An important issue is the nature of the most reactive amino functions in TNF. The inventors will approach this by N-terminal amino acid determination of either 1) native TNF, 2) moderately (1–3 residues) acetylated TNF, or 3) fully (~12 residues) acetylated TNF. If the N-terminal valine is most reactive, preparations 2 and 3 should give weak or no signals, depending on the exact extent of acetylation and induced heterogeneity. If a lysyl residue is the preferred initial target, preparations 1 and 2 should be comparable, and 3 should give an attenuated signal. If 3 gives a normal N-terminal valine signal, it would suggest that only the four lysyl residues per monomer are reactive under these conditions. Then the important conclusion would be that the SUV-$C_8$TNF preparations characterized to date do not display the TNF molecule in a manner oriented the way pro-TNF is displayed on the effector cell membrane.

The approaches the inventors have successfully employed for native TNF will be extended to the second-generation TNFs developed in Aim a. For example, as basic substitutions (Arg or Lys) or extensions are introduced in or to the flexible amino terminus which confer favorable biological characteristics (Aim d), opportunities to acylate new lysyl side chains or the new amino terminus arise. It is postulated that this approach will likely be successful as it may allow linkage to lipids in regions of the TNF variant less constrained by such considerations as receptor binding.

The approach discussed above appears to be highly feasible based on present experience with native TNF. The priority for selection of TNF variants will be based upon several factors, including their ease of development, biological properties as free entities, and a priori engineering of novel acylation-sites.

b.2. Myristylation in sit.

The vectorial display of pro-TNF in the effector cell membrane is such that the mature protein is linked via its amino-terminus to a ~20 amino acid segment and thereby to a transmembrane domain of ~25 residues. Although a definition of the amino groups most susceptible to acylation (Aim b. 1) has yet to be made and may include the N-terminal valine, some heterogeneity is almost a certainty, both with respect to site and number of residues. In order to present the mature protein in/on a liposome in an orientation similar to that found for the precursor, specific introduction of lipid at the N-terminus is desirable. The goal of this experiment is to achieve this via introduction of nucleotide sequences to the TNF cDNA which will encode a myristylation signal at this terminus. The inventors have avoided perturbation near the C-terminus such as palmitylation found in p21 Ras,[54] since in TNF this region appears to be bound by significant structural constraints.[34-55]

A general strategy for introducing a myristylation signal to a proto-oncogene product p21 Ras is described by Buss et al.[56] The inventors propose a modification of this general strategy in preparing TNF constructs. The first construct will be obtained by linking the cDNA encoding the first 11 amino acids of the amino- terminal sequences of RaSV[57] to that encoding the 157 amino acid mature TNF protein. The NIH/3T3 cell is an appropriate target for transfection, and the inventors may therefore employ the same protocol as has been employed for expressing both the full length parental pro-TNF cDNA as well as a mutant cDNA. In the referenced mutant cDNA, the transmembrane domain and the domain joining the transmembrane region to the mature protein are truncated. Successful cotransfection will be verified by conferred resistance to G418 and by Southern blotting with a $^{32}$p-labeled TNF probe available in Applicant's laboratory.

Expression of protein will be monitored in the supernatant by bioassay, ELISA, and immunoprecipitation/Western blotting, anticipating a product of ~18.5 kD. However, since the desired and anticipated localization is in the membrane, the inventors will be prepared to characterize the subcellular localization and trafficking of the putative lipoprotein. Protein will be labelled with $^3$H-leucine or $^{35}$S-cysteine (methionine is absent from the mature TNF) and myristylated adducts detected by metabolic labeling with $^3$H-myristic acid; crude membrane-containing fractions will be separated from cytosol by hypotonic lysis-ultracentrifugation. The inventors postulate that the myristylated protein, although synthesized in the cytosol, will be rapidly associated with the membrane. If the protein is indeed membrane-associated, its orientation may be opposite or the same as pro-TNF. This will be determined by the several approaches (i–iv) outlined below:

i. Proteolysis

Confluent radiolabelled 3T3 transfectants will be washed with DPBS and then subjected to trypsinization for various lengths of time at 37 ° C., predetermined to maintain cell viability. The supernatant and membrane fractions will be analyzed by immunoprecipitations/Western blotting, to assess cleavage of protein from the membrane-localized myristylated TNF. If this occurs, the pelletable extract should show a faster moving band that can be labeled through protein or lipid; the supernatant may reveal proteolytic fragments.

ii. Cell surface RIA

3T3 transfectants will be grown to confluence and subjected to chemical fixation with paraformaldehyde.[42,43,46] A primary rabbit anti-human TNF antiserum will be incubated at various dilutions on the fixed monolayer; a negative control will be the preimmune serum. The $^{125}$I-Protein A will be added to detect bound primary antibody, and a comparison will be made to both the negative control above and to a positive control, our 3T3 transfectant expressing normal pro-TNF with mature TNF in the lumen.

iii. Cell surface radioiodination

3T3 transfectants will be subjected to cell-surface radioiodination by the IODO-GEN procedure. The membrane fraction of radiolabeled cell lysates will be subjected to immuno-precipitation/Western blotting. If the myristylated TNF is oriented to the cytoplasm, no significant signal is postulated to exist. If, however, it is oriented to the lumen, a band at ~18.5 kD should be evident. The transfectant expressing the parental pro-TNF cDNA will be a positive control, and will display a radioiodinated band at 26 kD.

iv. Detection of cell surface protein using fluorescence activated cell sorter (FACS)

Confluent 3T3 transfectants will be washed with PBS and resuspended with 0.1 mM EDTA, pH 8. After another wash in PBS, the cells will be incubated with a primary monoclonal Ab against TNF then followed by a 30 min incubation with fluorescein isothiocyanate (FITC)—conjugated rabbit anti-mouse antibody. The percent positive fluorescence will be determined using an EPICS, Profile 1 fluorescence activated flow cytometer.

It is believed that the overall structure of this myristylated TNF construct will reflect the salient features of transmembrane pro-TNF. In the latter, the mature protein is linked via its amino terminus to the putative hydrophobic anchor with an ~20 amino acid domain; in the inventors construct, the mature protein may be similarly linked to the lipid group via a sequence of about 11 residues. However, other constructs may be envisioned which mimic this relationship more closely, including a similar extension of the leader sequence. In the studies of Buss et al[56] an 11 residue segment or the entire amino-terminus of RaSV (59 residues) was employed. Interestingly, either construct conferred the myristylation signal to a mutant p21 Ras gene product which allowed membrane binding; however, only the former and not the latter had transforming activity. These results may either be attributable to perturbed structure of the protein or to its altered interactions with membrane-associated targets.

Commercial Production:

It is submitted that myristylated-TNF adducts, produced by this strategy will be particularly suitable for non-bacterial (mammalian or yeast) expression systems, since bacteria do not recognize the same signals. Alternatively a method to produce TNF mutants with appropriate post-translational modifications which may be used in conjunction with the present invention is the baculovirus expression system in insect cells. This expression system has been successfully used for large scale expression of proteins with functional post-translational modification, which the bacterial expression system cannot do. The isolation procedure for such membrane-bound proteins must ultimately isolate these adducts in an environment free of contaminating agents and impurities, such as detergents, that would perturb liposomes of liposome binding, as required in Aim c.

b.3. Amino-terminal tailing with transmembrane sequences in situ

The rationale for this study is quite similar to that of Aim b.2: to present a lipophilic form of mature TNF in a fashion akin to that found on the monocyte/macrophage cell-surface. In this section, affinity for lipid membranes would be endowed on the TNF by amino acid sequences corresponding to the transmembrane domain of pro-TNF, putatively from residue –46 to –21. Since this domain is linked by a ~20 amino acid segment to the mature protein, and since this linker is subject to at least one protein, and since this linker is subject to at least one proteolytic event aside from the cleavage at –1, +1, the inventors will most preferably eliminate these susceptible sites in the presently proposed constructs. A most preferable construct would link the mature protein via its amino terminus to a hydrophobic stretch of amino acids, of minimal length necessary for stable display in the lipid membrane.

The initial strategy would be guided by the inventor's experience and development of a variant of pro-TNF, termed pMTpTNF OL1. The OL1 cDNA was in part designed to encode a TNF variant in which (1) the normal sequence of the mature protein is preserved, (2) approximately one-half (residues –32 to –21) of the putative transmembrane domain (–46 to –21) is eliminated and (3) the entire native linking sequence (–20 to –1) is replaced with four new residues, Ile-Asp-Leu-Glu, thereby eliminating known (–1, +1) and putative cleavage sites. Characterization of N1H/3T30L1 transfectants reveals that (1) by Southern blotting a truncated cDNA, corresponding to elimination of ~90 bp, is evident, (2) these transfectants are capable of acting as macrophage-like effector cells and lyse L929 cells in coculture, and (3) these transfectants release TNF-like activity into their supernatant.

c. Liposomal formulations of lipophilic TNFs produced by Aim b.

There are several tenets which will influence the strategy employed in this Aim. For example, it is known that monocytes/macrophages employ a membrane-form of TNF to kill tumor cells in a contact-dependent manner.[42-43,58] Whether the potent membrane-form of TNF is the transmembrane pro-TNF or mature TNF bound to its receptor, or both, is not certain. Some studies support the former mechanism.[44,45,46] While this issue remains to be resolved, there is no question that these effector cells are far more potent than even very high doses of TNF in their tumoricidal function. The inventors submit that presenting TNF linked to a liposome surface is an appropriate model with which to characterize the behavior of membrane-bound TNF.

Additionally, the ability to formulate TNF-liposomal preparations with high efficiency is essential for their further preclinical evaluation and, the eventual clinical application of such drug carrier-complexes. The previously reported studies of Debs et al.[5-6] employed MLV preparations which either encapsulated or displayed (associated) native rHuTNF. These preparations were constructed with only poor efficiency; for example, native TNF associated with preformed MLVs with an efficiency of only 3.9%. Furthermore, the stability of this and the other MLV-TNF preparations. TNF preparations to in vitro manipulations, such as physiological temperature or serum exposure, which might mimic the in vivo environment, was not reported. However, reduced toxicities and better lung and liver targeting[6] encourage further development of these TNF forms.

The inventors' priorities in this section will be dictated by a need for high efficiencies of formulation of liposomal TNF and by a desire to present the TNF on the liposome surface. The inventors propose to achieve this by selective introduction and orientation of lipophilic arms to mature TNF or second-generation TNFs (Aims a and b) to enhance formulation efficiency. In addition, the use of SUVs as carriers, which are better able to avoid capture by the RES than MLVs and may be more capable of encounters with tumor cells, will be the initial focus. However, in some situations facilitated RES-mediated uptake of liposomal-TNF may be desirable, and therefore MLV formulations may also be developed as part of these studies.

The inventors' initial experiments have employed lipophilic TNFs, generated according to Aim b.1., and SUVs of DPPC. These formulations were prepared with high efficiency at ambient temperature and were stable to storage in DPBS over several days, still retaining binding interactions as determined by molecular sieving. Although DPPC in MLVs has a phase-transition temperature of ~41 °C., in an SUV this drops to ~37° C., perhaps due to the destabilizing effects of high curvature. When SUV-$C_8$-TNF was subjected to re-chromatography at 37° C. in DPBS, significant loss of binding was observed.

Although a major tenet which influences the strategy discussed above is that the liposome should present the TNF to the target in a vectorial, membrane-environment, akin to the monocyte/macrophage effector cell, the inventors envision that actual mechanisms in vivo may alternatively be that liposome-entrapped TNF may also be an effective mode of delivery. The influence of increased lipophilicity of TNF on its encapsulation efficiency in MLVs may therefore also be examined as part of the inventors' studies. Debs and co-workers reported that native TNF could be encapsulated in MLVs with efficiencies that ranged from 2.0–11.4%, depending on the lipid composition.[5] These low efficiencies were determined for a single reaction condition of mass ratio of lipid to protein. The inventors propose that lipophilic TNFs may be encapsulated or associated with liposome (MLVs or SUVs) with much higher efficiencies than this. In addition, the actual protein to lipid ratio of the preparation itself is important. The inventors propose to alter the coupling conditions to increase the protein/lipid ratio, to determine when the amount of protein encapsulated will plateau. The selection of particular TNFs proposed from Aim b. may additionally be evaluated in light of the results of prescreening of these variants in Aim d. Priorities for further development of liposomal-TNFs produced in this study may in turn be influenced by parameters of formulation efficiency and stability.

d. In vitro evaluation of TNFs in efficacy and toxicity models

This study may be fully integrated with the preceding three studies. For example, second-generation TNFs produced in Aim a. may be screened. Those second generation TNFs with the most promising potency and toxicity characteristics will receive the highest priority for development in Aim b. Upon screening the lipophilic variants from Aim b., the most promising and feasible candidates may then be prepared as liposomal formulations in Aim c. These, in turn, may then be evaluated as set forth herein for their efficacy and toxicity.

The efficacy of these preparations may be assessed in part in terms of specific activity with a standard actinomycin D-treated L929 cell bioassay. In addition, the activity expressed in assays employing a panel of tumor cell targets, including those resistant to normal, mature TNF may be determined.

The toxicity of these preparations may further be evaluated in in vitro models of hypotension and cachexia. The former side-effect is the dose-limiting toxicity observed to date in the Phase I/Phase II clinical trails. The molecular basis for this phenomenon is currently under intense investigation, but the following in vivo model can be proposed to embody the most salient feature described in vitro. TNF in conjunction with other cytokines, e.g. IFN-gamma, activates the endogenous nitric oxide synthetase pathway in endothelial cells.[41] Nitric oxide has been shown to be equivalent to endothelium-derived relaxing factor,[39,40] which results in their morphological and functional alterations. The most relevant of these is perturbation of junctions between neighboring endothelial cells, ultimately resulting in pulmonary edema and hypotension. It is the inventors' purpose to develop TNF variants or liposomal formulations which can exert strong tumoricidal effects in vitro and have minimal effects in the endothelial cell toxicity model. It remains to be determined if these characteristics can be structurally dissociated; however, Kamijo and co-workers have shown that cytotoxicity, receptor binding and differentiation-inducing activity did not correlate and therefore were dissociable characteristics in a series of TNF mutants they developed.

Finally, since TNF and cachectin are identical, the inventors may then assess the activity of TNF variants and liposomal formulations in 3T3-L1 adipocytes for their inhibitory effects on lipoprotein lipase and stimulatory effects on lipolysis. An experimental model for examining lipoprotein lysase and lipolysis activity is described by Fielding et al[59] and Kawakami et al,[60] which references are specifically incorporated herein for this purpose.

d.1. Efficacy

The TNF preparations from the above experiments will first be evaluated for their specific activity in the standard, actinomycin D-treated L-929 target cell bioassay, as the inventors are currently doing for their adducts generated from Aim b.1. and their liposomal formulations from Aim c. Mature TNF is less potent in this assay than the TNF variant, TNF-$S_{AM2}$; this has in turn been found to correlate with their relative potency in other assays employing normally TNF-resistant murine EMT-6 mammary adenocarcinoma cells in conjunction with hyperthermia.

The in vitro cytotoxic efficacy will also be evaluated using a panel of rodent and human normal and tumor cells which differ in their sensitivity to parental TNF.[52] The inventors propose to evaluate in particular those human cell lines representative of the important lung, colon and breast tumors. By way of example, these cell lines include the A-549 lung and LS174T and WIDr colon lines.[26] The inventors may then add to this the MCF-7 breast line,[30] and the colon lines Colo 205 and Ca-Co-2. The latter are of particular interest because the inventors have found that their normally TNF-resistant phenotype can be reversed synergistically by treatment with Cis- or Carbo-platinum and/or acute hyperthermia along with TNF.

d.2. Toxicity d.2.i. Hypotension-Endothelial cell model

This model for TNF-mediated effects resulting in hypotension will initially employ an endothelial cell experimental model. The Kilbourn[41] reference is specifically incorporated herein by reference for the purpose of providing the general aspects of measuring hypotension with an endothelial cell model. The endothelial cells may be obtained from the bovine aorta, a line available from ATCC. The inventors propose to incubate this cell line with TNF, or second- generation TNFs, or their lipophilic modifications, or, in turn, their liposomal formulations and sensitizing doses of recombinant IFN-gamma. One particular endpoint to be measured may be the accumulated nitrite from activation of the nitric oxide synthetase pathway. Dose-response curves will be established for each test preparation. The most favorable outcome will be a shift in these curves to lower nitrite production per mass of test TNF compared to parental TNF. Other endothelial cell models will also be examined, including human liver endothelial cell lines currently being established in collaboration with Dr. Mark Roh, Assistant Professor of Surgery of our institution.

d.2.ii. Cachexia model

The inventors will employ the procedures of Kawakami et al so and Soma et al[27] The effects of the TNF preparation on suppression of lipoprotein lipase and stimulation of lipolysis will be evaluated in 3T3-L1/adipocytes. Soma and co-workers predicted from these two in vitro assays that TNF-$S_{AM2}$ should have lower cachectic activity than either parental TNF or two other TNF variants, $S_{AM3}$ and $S_{AM4}$.[27] Interestingly, when the acute toxicities of these four TNFs were determined in mice, TNF-$S_{AM2}$ was the least toxic; however, parental TNF was more toxic than the two other TNFs.

In summary, the experiments outlined above are proposed to provide a measure of the efficacy of the claimed preparations from the in vitro tumor toxicity results obtained. Second-generation TNFs found to be most promising (i.e., most highly active, especially as against tumor cell lines resistant to parental TNF and of lesser activity in the endothelial cell assay) will then be proposed for use as treatments for human tumors (Prophetic Example 9).

EXAMPLE 9

Proposed In Vivo Use of Liposomal-Lipophilic TNF in Humans

The present example is provided to present a protocol by which the liposomal-lipophilic tumor necrosis factor preparations disclosed herein may be used in humans, most particularly to reduce and/or halt tumor growth rate, as well as effect a disintegration of tumors already existing, in vivo.

Formulations of both modified TNF-SUVs and modified TNF-MLVs are submitted to provide anti-tumor and anti-cancer effects. The selection of modified TNF-SUVs or modified TNF-MLVs will require consideration of the particular condition of the patient to be treated and of the disposition of the tumor being treated. For example, where the tumor is already highly infiltrated with phagocytic cells, then the use of a modified TNF-MLV preparation would be advantageously used to deliver TNF to phagocytic-rich tissues. Such is expected to provide an effective method of TNF delivery to the tumor. Alternatively, modified TNF-SUV preparations would most preferably and advantageously be used in the treatment of a patient who does not have a tumor which is highly infiltrated with phagocytic cells. These preferred mechanisms take advantage of the body's normal physiological trafficking of molecules to various tissues, etc. 1.0 Modified TNF-MLV preparations are hypothesized to reduce toxic side effects associated with TNF in vivo as the enhanced binding efficacy of the modified TNF (having increased hydrophobicity) assures that only relatively small amounts of the administered TNF is present in a free, unbound form in the circulation. As already described, the modifications of TNF described herein so affect the TNF molecule that essentially all of the modified TNF molecules associate with the liposome, whether the liposome be an SUV or MLV.

The reduced size of the liposomes used in the modified tumor necrosis factor preparations, particularly described as small unilamellar vesicles (SUVs) claimed herein, are better able to avoid capture by RES. This advantage is hypothesized by the inventors to increase the opportunities for liposome-tumor cell encounters when the preparation is administered systemically. Such would overcome limitations previously reported using larger MLV preparations.[6]

Additionally, the disclosed formulation of small unilamellar liposomes presenting tumor necrosis factor on their outer surfaces is further hypothesized to provide the advantage of better mimicking the mode of delivery employed in nature by activated monocytes/macrophages in tumoricidal reactions already observed in vitro. However, modified TNF encapsulated in MLVs would be equally as effective in providing the described therapeutic benefits, and may even be preferred in the treatment of some patients whose tumors are already highly infiltrated with phagocytic cells. For example, modified TNF-MLVs would advantageously become carried to tumorous tissue beds, or delivered by regional administration.

According to the one proposed therapeutic use of the present TNF-formulation, the lipophilic liposomal TNF agents are administered systemically to a patient having a TNF-responsive tumor. Periodic doses of the liposomal lipophilic TNF preparation would continually be administered to the patient until an improvement in the patients condition, indicated for example by a reduction in tumor size, could be detected. Clinical trials and animal studies are being conducted so as to establish more precise doses of the TNF-preparations and more particularly defined treatment regimens to be used. Additionally, the introduction of liposomal TNF as a clinical tool in the treatment of tumors and as an anti-cancer agent may also be initiated using the described strategies.

In several cilinical trials, regional administration of tumor necrosis factor of the present invention resulted in efficacy/toxicity paramaters superior to those observed with systemic administration. To achieve an intratumoral accumulation and a "depo" effect, a liposomal formulation of acylated TNF, TNF-Sam2, which has a superior therapeutic index to TNF-$\alpha$, was employed. Free TNF-$\alpha$ and TNF-Sam2 was compared with liposomal TNF-Sam2 covalently modified with caprylic acid in a canine model for cytokine-induced hypotension, and in a murine syngenic tumor model. All TNF formulations induced tachycardia and decreased systemic vascular resistance. Free TNF-$\alpha$ caused marked hypotension and arterial hypoxemia. Liposomal-C8-TNF-Sam2 caused only mild or no hypotension. The liposomal C8-TNF-Sam2 induced a prolonged control of tumor growth in mice bearing Meth A sarcoma s.c. Durable growth control was investigated with i.d. administration of the TNF formulation, which was less satisfactory in these specific applications. Reference is made to *Proceedings of the American Association for Cancer Research, Immunology/Biological Therapy*, "Improved therapeutic Index of a liposomal lipophilic tumor necrosis factor mutant." Klostergaard, et al., 35:3098 (1994).

In some embodiments., regional administration encompasses infusion of therapeutic agent "up stream" of the site of treatment, and optionally includes, a "down stream" removal or reduction of therapeutic agent.

REFERENCES

The following references are specifically incorporated herein by reference in pertinent part for the particular purposes as indicated throughout the present application.

1. Decker et al. (1987), *J. Immunol.*, 138(3):957–62.
2. Espevik et al. (1987), *Immunology*, 61:443–8.
3. Bakouche et al. (1988), *J. Immunol.*, 140:1142–7.
4. Kriegler et al. (1988), *Cell*, 53:45–53.
5. Debs et al. (1989), *J. Immunol.*, 413:1192–7.
6. Debs et al. (1990), *Cancer Res.*, 50:375–80.
7. Utsumi et al. (1988), *FEBS Letters*, 238(1): 13–6.
8. Utsumi et al. (1990), *Agric. Bio. Chem.*, 54(1):25–30.

9. Ando et al. (1990), *FEBS Letters,* 240(1,2):216–20.
10. Terada (1988), *Cell Structure and Function,* 13:359–71.
11. WPI Acc No:89-311120/43 (EP 89 302712)—Sherwin, S. A. (1988)
12. Old (1985) *Science,* 230:630–632.
13. Oliff et al. (1987), *Cell,* 50:555–563.
14. Zimmerman et al. (1989), *Cancer Res.,* 49:6521–6528.
15. Knauf et al. (1988), *J. Biol. Chem.,* 263:15064–15070.
16. Katre et al. (1987), *Proc. Natl. Acad. Sci. USA,* 84:1487–1491.
17. Goodson et al. (1990), Biotechnology, 8:343–356.
18. Davis et al. (1980), *In: Biomedical Polymers,* p. 441. Academic Press, New York.
19. Katre, N. V. (1990), *J. Immunol.,* 144:209–213.
20. Old (1990), *In: Tumor Necrosis Factor: Structure, Mechanism of Action, Role in Disease and Therapy,* p. 1 (Karger, Basel).
21. Fransen et al. (1985), *Nucleic Acid Research,* 13:4417–4429.
22. Pennica et al. (1985), *Proc. Natl. Acad. Sci., USA,* 82:6060–6064.
23. Kull et al. (1984), *Proc. Natl. Acad. Sci., USA,* 81:7932–7936.
24. Itoh et al. (1986), *J. Biochem.,* 99:9–15.
25. Eck et al. (1988), *J. Biol. Chem.,* 263:12816–12819.
26. Soma et al. (1987), *Biochem. Biophys. Res. Commun.,* 148:629–635.
27. Soma et al. (1988), *J. Biol. Resp. Mod.,* 7:587–795.
28. Gatanaga et al. (1989), *J. Biol. Resp. Mod.,* 8:278–286.
29. Armstrong et al. (1985), *J. Natl. Cancer Inst.,* 74:1–9.
30. Creasey et al. (1987), *Cancer Res.,* 47:145–149.
31. Kamijo et al. (1989), *Biochem Biophys. Res. Commun.,* 160:820–827.
32. Carswell et al. (1975), *Proc. Natl. Acad. Sci, USA,* 72:3666–3670.
33. Beautler et al. (1986), *Nature,* 320:584–589.
34. Oettgen et al. (1987), *In: Important Advances in Oncology, Philadelphia,* J. B. Lippincott Co., 105–130.
35. Blick et al. (1987), *Cancer Res.,* 47:2986–2989.
36. Klausner A. (1987), *Biotechnology,* 5:335–341.
37. Taguchi, T. (1986), *Jpn. J. Cancer Chemother.,* 13:3491–3498.
38. Kilbourn et al. (1990), *Proc. Natl. Acad. Sci., USA,* 87:3629–3632.
39. Palmer et al. (1988), *Nature,* 333:664–666.
40. Ignarro et al. (1987), *Proc. Natl. Acad. Sci., USA,* 84:9265–9269.
41. Kilbourn et al. (1990), *J. Natl. Cancer Inst.,* 82:772–776.
42. Klostergaard et al. (1990), *J. Leukocyte Biol.,* 48:220–228.
43. Decker et al. (1987), *J. Immunol.,* 138:957–961.
44. Kriegler (1988) *Cell,* 53:45–53.
45. Luettig et al. (1989), *J. Immunol.,* 143:4034–4038.
46. Espevick et al. (1987), *Immunol.,* 61:443–448.
47. Jones et al. (1989), *Nature,* 338:225–228.
48. Klostergaard et al. (1987), *Cancer Res.,* 47:2014–2020.
49. Lapidot et al. (1967), *J. Lipid Res.,* 8:142–145.
50. Remick et al. (1987), *Lab Invest.,* 56:503–590.
51. Tracey et al. (1986), *Science,* 234:470–474.
52. Shepard (1988), *J. Clin. Immunol.,* 8:333–341.
53. Shortie et al. (1982), *Procl Natl. Acad. Sci., USA,* 77:5375–5379.
54. Willumsen et al. (1984), *Nature,* 310:583–585.
55. Soma (1990), *J. Clin. Exp. Med.,* 152:589–593.
56. Buss et al. (1989), *Science,* 243:1600–1603.
57. Rasheed et al. (1983), *Science,* 221:155–158.
58. Roh et al. (1990), *Surgery,* 108:400–405.
59. Fielding et al. (1977), *Arach. Pathol. Lab. Med.,* 101:225–229.
60. Kawakami et al, (1987), *J. Biochem.,* 101:331–338.

---

What is claimed is:

1. A modified TNF having cytolytic activity wherein amino residues of the tumor necrosis factor are modified to include fatty acids, such that binding between the modified TNF and a liposome is enhanced.

2. The modified TNF of claim 1 wherein an N-terminal amino group or a lysine amino group of the tumor necrosis factor is modified.

3. The modified TNF of claim 1 or 2 wherein 1 to about 5 amino residues of the tumor necrosis factor are modified to include fatty acids.

4. The modified TNF of claim 3 wherein between 1 to about 3 amino residues of the TNF are modified to include fatty acids.

5. The modified TNF of claim 4 wherein the modified amino residues are lysine amino residues.

6. The modified TNF of claim 5 wherein the modified amino residues of the TNF include lysyl side chains linking the fatty acid to the tumor necrosis factor.

7. The modified TNF of claim 4 wherein the fatty acids bind the TNF to a liposome to provide a liposomal lipophilic TNF.

8. The modified TNF of claim 7 wherein the fatty acid at the TNF lysyl side chain is capable of associating the TNF with the liposome with at least 50% efficiency.

9. The modified TNF of claim 8 wherein the liposome is a small unilamellar vesicle or a multilamellar vesicle.

10. The modified TNF of claim 7 wherein the TNF is associated at liposome surfaces or encapsulated within the liposome.

11. The modified TNF of claim 7 wherein the liposome is comprised of a phospholipid.

12. The modified TNF of claim 11 wherein the phospholipid is a DSPC or DPPS.

13. An rHuTNF preparation having 1 to about 5 modified amino residues, said amino residues further modified to include fatty acids, said rHuTNF preparation capable of associating with a liposome with 100% binding efficiency.

14. The rHuTNF preparation of claim 13 having between 1 to about 3 modified amino residues.

15. A method for preparing liposomal lipophilic TNF with between 50%–100% binding efficiency, said method comprising the steps of:

reacting an mount of tumor necrosis factor with a sufficient amount of an N- hydroxysuccinimide ester of a fatty acid for an mount of time sufficient to form a volume of a lipophilic TNF preparation;

formulating a volume of liposomes capable of binding lipophilic TNF molecules with high efficiency; and incubating a volume of the liposomes with a sufficient amount of lipophilic TNF preparation for an mount of time sufficient for the lipophilic TNF to bind the liposomes to provide a formulation of liposomal-lipophilic tumor necrosis factor.

16. The method of claim 15 wherein the tumor necrosis factor is a recombinant human tumor necrosis factor.

17. The method of claim 15 wherein the fatty acid comprises fatty acids having a carbon chain length of between 8 to 14 carbon atoms.

18. The method of claim 15 wherein the tumor necrosis factor is reacted with the N-hydroxysuccinimide esters of fatty acids at about 26° C. for about 3 hours.

19. The method of claim 15 wherein the liposomes are comprised of a neutral lipid.

20. The method of claim 19 wherein the neutral lipid is a phospholipid.

21. The method of claim 20 wherein the phospholipid is DPPC or DSPC.

22. The method of claim 20 wherein the liposomes have a diameter of between 0.02- 0.05 μm.

23. The method of claim 15 wherein the liposomal-associated tumor necrosis factor preparation comprises a ratio of about 0.5 moles tumor necrosis factor per mole of liposomal preparation.

24. The method of claim 15 wherein the modified liposomal lipophilic tumor necrosis factor is associated with a surface of the liposome.

25. A pharmacologically acceptable preparation of tumor necrosis factor comprising modified tumor necrosis factor molecules linked to a liposome surface, wherein said tumor necrosis factor is modified to include fatty acids.

26. The pharmacologically acceptable preparation of tumor necrosis factor of claim 25 wherein the liposomes are small unilamellar or multilamellar vesicles having a diameter of about 0.02–0.05 μm.

27. The pharmacologically acceptable preparation of tumor necrosis factor of claim 25 wherein the tumor necrosis factor molecules include modified amino residues to include fatty acids.

28. The pharmacologically acceptable preparation of tumor necrosis factor of claim 27 wherein 1 to about 5 amino residues of the tumor necrosis factor are modified to include a fatty acid.

29. The pharmacologically acceptable preparation of tumor necrosis factor of claim 25 wherein between 1 to about 3 amino residues of the tumor necrosis factor are modified to include a fatty acid.

30. The pharmacologically acceptable preparation of tumor necrosis factor of claim 25 wherein the modified tumor necrosis factor molecules include fatty acids having a carbon chain length of between 8 to 14 carbons.

31. The pharmacologically acceptable preparation of tumor necrosis factor of claim 30 wherein the fatty acid is caprylic acid, capric acid, lauric acid or myristic acid.

32. The pharmacologically acceptable preparation of tumor necrosis factor of claim 30 wherein the fatty acid is caprylic acid.

33. A method for treating a tumor in a patient, said method comprising:

identifying a patient having a tumor necrosis factor receptive tumor;

administering to the patient a tumor-inhibiting dose of a liposomal-lipophilic modified tumor necrosis factor preparation; and treating the patient with daily tumor-inhibiting doses of the liposomal-lipophilic modified tumor necrosis factor until an improvement in the patient's condition is detected.

34. The method of claim 33 wherein the liposomal-lipophilic modified tumor necrosis factor comprises a tumor necrosis factor molecule modified at less than 5 amino residues to include a fatty acid, said fatty acid comprising a carbon chain length of between 8–14 carbons.

35. The method of claim 33 wherein the liposomal-lipophilic modified tumor necrosis factor comprises a tumor necrosis factor modified at between 1 to about 3 amino resides.

36. The method of claim 35 wherein the 1–3 amino residues of modified tumor necrosis factor include a fatty acid having a carbon chain length of 8 carbons.

37. The method of claim 36 wherein the fatty acid is caprylic acid.

38. The method of claim 33 wherein the liposomal-lipophilic modified tumor necrosis factor comprises a liposome with modified tumor necrosis factor associated with its surface, said liposome comprising a small unilamellar vesicle.

39. The method of claim 33 wherein the administration of the liposomal-lipophilic modified tumor necrosis factor is systemic.

40. The method of claim 33 wherein the administration of the liposomal-lipophilic modified tumor necrosis factor is local.

41. The method of claim 33 wherein the liposomal lipophilic modified tumor necrosis factor comprises a tumor necrosis factor molecule modified at an N terminal amino group or a lysine amino group to include fatty acids.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Val  Arg  Ser  Ser  Ser  Arg  Thr  Pro  Ser  Asp  Lys
1              5                             10
```

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

-continued

Arg Ile Arg Met
1

( 2 ) INFORMATION FOR SEQ ID NO:3:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

Lys Ile Lys Met
1